US012042392B2

(12) United States Patent
Axelson, Jr. et al.

(10) Patent No.: US 12,042,392 B2
(45) Date of Patent: Jul. 23, 2024

(54) SHOULDER IMPLANT COMPONENTS

(71) Applicant: Encore Medical, L.P., Austin, TX (US)

(72) Inventors: Stuart L. Axelson, Jr., Succasunna, NJ (US); Andrew M. Dickson, Austin, TX (US); Kirstin Widding, Austin, TX (US); Joseph Albert Abboud, Bryn Mawr, PA (US); Surena Namdari, Gladwyne, PA (US); Mark Alan Frankle, Tampa, FL (US); Jonathan C. Levy, Fort Lauderdale, FL (US); Gerald Ross Williams, Jr., Villanova, PA (US); Nathan Oliver Plowman, Wellsville, UT (US); Richard Justin Hyer, Hyrum, UT (US)

(73) Assignee: ENCORE MEDICAL, L.P., Austin, TX (US)

( * ) Notice: Subject to any disclaimer, the term of this patent is extended or adjusted under 35 U.S.C. 154(b) by 515 days.

(21) Appl. No.: 16/729,204

(22) Filed: Dec. 27, 2019

(65) Prior Publication Data
US 2020/0129301 A1 Apr. 30, 2020

Related U.S. Application Data

(63) Continuation of application No. 15/874,091, filed on Jan. 18, 2018, now Pat. No. 10,561,501.
(Continued)

(51) Int. Cl.
*A61F 2/40* (2006.01)
*A61F 2/30* (2006.01)
*A61F 2/46* (2006.01)
(52) U.S. Cl.
CPC .......... *A61F 2/4014* (2013.01); *A61F 2/4059* (2013.01); *A61F 2/4081* (2013.01);
(Continued)

(58) Field of Classification Search
CPC ............ A61F 2/4059; A61F 2002/4062; A61F 2002/4066; A61F 2002/407
See application file for complete search history.

(56) References Cited

U.S. PATENT DOCUMENTS 4,608,053 A * 8/1986 Keller ................. A61F 2/30728
623/23.31
4,728,334 A * 3/1988 Spotorno ............ A61F 2/30771
623/23.31
(Continued)

FOREIGN PATENT DOCUMENTS

CN 101340862 A 1/2009
CN 105377195 A 3/2016
(Continued)

OTHER PUBLICATIONS

Notice of Reasons for Refusal in Japanese Patent Application No. JP 2019-539207, mailed Jan. 4, 2022 (4 pages w/English translation).
(Continued)

*Primary Examiner* — Megan Y Wolf
(74) *Attorney, Agent, or Firm* — Nixon Peabody LLP

(57) ABSTRACT

A shoulder implant system includes a humeral stem implant, a humeral neck implant component, a humeral head implant component, and a glenoid implant. The humeral stem implant has a fin coupled to an exterior surface thereof that is inwardly tapered at an angle relative to vertical. At least a portion of the fin forms a wedge that directly engages and compacts cancellous bone during installation of the humeral stem implant. The humeral neck implant component is configured to be coupled with the humeral stem implant. The humeral head implant component is configured to be coupled to the humeral stem implant via the humeral neck implant component. The glenoid implant has a plurality of
(Continued)

peripheral pegs. Each of the peripheral pegs has a plurality of sets of resilient lobes.

18 Claims, 21 Drawing Sheets

Related U.S. Application Data

(60) Provisional application No. 62/448,205, filed on Jan. 19, 2017.

(52) U.S. Cl.
CPC ............. *A61F 2002/30171* (2013.01); *A61F 2002/30822* (2013.01); *A61F 2002/30878* (2013.01); *A61F 2002/30881* (2013.01); *A61F 2002/30884* (2013.01); *A61F 2002/30892* (2013.01); *A61F 2002/30897* (2013.01); *A61F 2002/4037* (2013.01); *A61F 2002/4044* (2013.01); *A61F 2002/4062* (2013.01); *A61F 2/4612* (2013.01)

(56) References Cited

U.S. PATENT DOCUMENTS

| | | | |
|---|---|---|---|
| 4,919,670 | A | 4/1990 | Dale |
| 5,032,132 | A | 7/1991 | Matsen, III |
| 5,507,817 | A * | 4/1996 | Craig .................. A61F 2/4014 623/20.11 |
| 6,168,632 | B1 * | 1/2001 | Moser ................ A61F 2/30771 623/23.31 |
| 6,436,148 | B1 * | 8/2002 | DeCarlo, Jr. ....... A61F 2/30771 623/23.15 |
| 6,911,047 | B2 | 6/2005 | Rockwood, Jr. |
| 7,160,328 | B2 | 1/2007 | Rockwood, Jr. |
| 9,226,830 | B2 | 1/2016 | de Wilde |
| 2005/0177241 | A1 | 8/2005 | Angibaud |
| 2007/0142917 | A1 | 6/2007 | Roche |
| 2009/0125113 | A1 | 5/2009 | Guederian |
| 2010/0228352 | A1 | 9/2010 | Courtney, Jr. |
| 2012/0130499 | A1 | 5/2012 | Long |
| 2012/0239155 | A1 | 9/2012 | De Wilde |
| 2013/0150972 | A1 | 6/2013 | Iannotti |
| 2014/0005789 | A1 | 1/2014 | Chavarria |
| 2014/0031945 | A1 | 1/2014 | Baptista |
| 2014/0257495 | A1 | 9/2014 | Goldberg |
| 2015/0150688 | A1 | 6/2015 | Vanasse |
| 2015/0272741 | A1 | 10/2015 | Taylor |
| 2016/0151164 | A1 | 6/2016 | Taylor |
| 2016/0206436 | A1 | 7/2016 | Chavarria |
| 2016/0367371 | A1 | 12/2016 | de Beaubien |
| 2016/0367375 | A1 | 12/2016 | Boulris |
| 2018/0000598 | A1 * | 1/2018 | Amis .................... A61F 2/3672 |

FOREIGN PATENT DOCUMENTS

| | | | |
|---|---|---|---|
| CN | 105796213 | A | 7/2016 |
| EP | 0761183 | A2 | 3/1997 |
| EP | 1048274 | A2 | 11/2000 |
| FR | 3013211 | A1 | 5/2015 |
| JP | 2014-515642 | A | 7/2014 |
| JP | 2016513498 | A | 5/2016 |
| JP | 2017523872 | A | 8/2017 |
| WO | WO-2004105654 | A1 * | 12/2004 ......... A61F 2/30771 |
| WO | 2014138424 | A1 | 9/2014 |
| WO | WO 2015/066608 | A1 | 5/2015 |
| WO | 2016025378 | A1 | 2/2016 |
| WO | WO 2016/114880 | A1 | 7/2016 |
| WO | 2018189322 | A1 | 10/2018 |
| WO | 2019006205 | A1 | 1/2019 |

OTHER PUBLICATIONS

First Examination Report in Indian Patent Application No. IN 201917033234, mailed Dec. 28, 2021 (6 pages).

International Search Report in International Patent Application No. PCT/US2018/014248, mailed Aug. 30, 2018 (7 pages).

Written Opinion in International Patent Application No. PCT/US2018/014248, mailed Aug. 30, 2018 (11 pages).

Extended Search Report in European Patent Application No. 21161485.4, dated May 19, 2021 (9 pages).

Request for Submission of an Opinion in Korean Patent Application No. KR 10-2019-7023995, mailed Aug. 16, 2022 (13 pages w/English translation).

* cited by examiner

SHOULDER IMPLANT COMPONENTS

CROSS-REFERENCE TO RELATED APPLICATIONS

This application is a continuation of U.S. patent application Ser. No. 15/874,091, filed on Jan. 18, 2018, now U.S. Pat. No. 10,561,501, which claims the benefit of and priority to U.S. Provisional Application No. 62/448,205, filed Jan. 19, 2017, each of which is hereby incorporated by reference herein in its entirety.

COPYRIGHT

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

The present disclosure relates generally to shoulder implant systems and, more particularly, to a shoulder implant systems with a humeral stem implant and a glenoid implant.

BACKGROUND

People experiencing shoulder joint pain can find relief by way of a shoulder replacement surgery that replaces one or more portions of the person's anatomy with one or more implant components. In some such cases, an upper portion of a patient's humerus (e.g., a portion of the humeral head) is cut. Then the humerus is cored and prepped to receive a stem implant therein. Some prior stem implants have a relatively long body that enters into the diaphysis region of the humerus to aid in aligning the stem implant during installation and can thus end up engaging the cortical bone, which can be undesirable.

The stem implant is inserted/installed in the prepped humerus and coupled with a humeral neck implant component and a humeral head implant component, the combination thus generally replacing the natural humeral head of the patient's humerus.

In some patients, the glenoid of the patient is replaced by a glenoid implant for the humeral head implant component to bear against during movement of the patient's arm. Prior glenoid implants typically require the patient's glenoid to be prepped by shaving the surface and drilling a set of bores or holes therein to receive pegs of the glenoid implant to aid in retaining the glenoid implant in place. The glenoid implant is typically cemented in place by a surgeon positioning the glenoid implant in place and holding it there until the bone cement cures.

The present disclosure is directed at solving and/or improving the above noted deficiencies along with solving other problems.

SUMMARY OF THE INVENTION

According to some implementations of the present disclosure, a humeral stem implant includes a lower stem portion, an upper stem portion, a first pair of fins, and a second pair of fins. The lower stem portion has a central axis. The upper stem portion extends from the lower stem portion and has a tapered face that is angled relative to the central axis of the lower stem portion. The first pair of fins extends from an exterior surface of the upper stem portion for providing rotational stability to the humeral stem implant by engaging cancellous bone. The second pair of fins extends from the exterior surface of the upper stem portion for providing rotational stability to the humeral stem implant by engaging cancellous bone. The second pair of fins is generally located on an opposite side of the upper stem portion relative to the first pair of fins.

According to some implementations of the present disclosure, a humeral stem implant includes a lower stem portion, an upper stem portion, a first pair of parallel fins, and a second pair of parallel fins. The lower stem portion has a central axis. The upper stem portion extends from the lower stem portion and has a tapered face that is angled relative to the central axis of the lower stem portion. The first pair of parallel fins is coupled to a posterior portion of an exterior surface of the upper stem portion. The second pair of parallel fins is coupled to an anterior portion of the exterior surface of the upper stem portion. The first pair of parallel fins and the second pair of parallel fins are configured to provide rotational stability to the humeral stem implant by directly engaging cancellous bone responsive to the humeral stem implant being seated in a humeral canal of a prepared humerus bone of a patient.

According to some implementations of the present disclosure, a humeral stem implant includes a lower stem portion, an upper stem portion, a first longitudinal fin, a second longitudinal fin, and a biologic ingrowth coating. The lower stem portion has a central axis. The upper stem portion extends from the lower stem portion and has a tapered face that is angled relative to the central axis of the lower stem portion. The first longitudinal fin has a first central axis and a first length and is coupled to a posterior portion of an exterior surface of the upper stem portion such that the first longitudinal fin forms a first window that is configured to receive a suture therethrough. The first longitudinal fin tapers inwardly such that the first central axis is at a first angle relative to the central axis of the lower stem portion. The second longitudinal fin has a second central axis and a second length and is coupled to the posterior portion of the exterior surface of the upper stem portion such that the second longitudinal fin forms a second window that is configured to receive a suture therethrough. The second longitudinal fin tapers inwardly such that the second central axis is at a second angle relative to the central axis of the lower stem portion. The second angle is different than the first angle. The second length is less than half of the first length. The first longitudinal fin and the second longitudinal fin are configured to provide rotational stability to the humeral stem implant by directly engaging cancellous bone responsive to the humeral stem implant being seated in a humeral canal of a prepared humerus bone of a patient. The biologic ingrowth coating is attached to a majority portion of the exterior surface of the upper stem portion such that the biologic ingrowth coating extends downward from the tapered face at least one millimeter beyond the first longitudinal fin.

According to some implementations of the present disclosure, a humeral stem implant includes a lower stem portion, an upper stem portion, and an elongated fin. The lower stem portion has a central axis. The upper stem portion extends from the lower stem portion and has a tapered face that is angled relative to the central axis of the lower stem portion. The elongated fin is coupled to an exterior surface of the upper stem portion. The elongated fin is inwardly tapered at an angle relative to the central axis of the lower stem portion. At least a portion of the elongated fin forms a wedge that directly engages and compacts cancellous bone during installation of the humeral stem implant.

According to some implementations of the present disclosure, a glenoid implant that is to be coupled with a prepared glenoid of a patient includes a body, a central peg, and a peripheral peg. The body has a concave surface configured to engage a humeral head implant component, and a convex surface configured to engage a mating surface of the prepared glenoid of the patient. The convex surface has a peripheral area surrounding a central area. The central peg extends from the central area of the convex surface. The central peg is configured to be cemented to a central bore of the prepared glenoid of the patient. The peripheral peg extends from the peripheral area of the convex surface. The peripheral peg has a first set of resilient lobes at a first longitudinal position of the peripheral peg and a second set of resilient lobes at a second longitudinal position of the peripheral peg that is spaced from the first longitudinal position.

According to some implementations of the present disclosure, a glenoid implant is provided that is to be coupled with a prepared glenoid of a patient. The prepared glenoid has a mating surface, a central bore, and a peripheral bore. The glenoid implant includes a body, a central peg, and a peripheral peg. The body has a concave surface configured to engage a humeral head implant component, and a convex surface configured to engage the mating surface of the prepared glenoid of the patient. The convex surface has a peripheral area surrounding a central area. The central peg extends from the central area of the convex surface. The central peg is configured to be cemented to the central bore of the prepared glenoid of the patient. The peripheral peg extends from the peripheral area of the convex surface. The peripheral peg has a first radially extending feature positioned at a first longitudinal position of the peripheral peg and a second radially extending feature positioned at a second longitudinal position of the peripheral peg that is spaced from the first longitudinal position. The first radially extending feature has three lobes that are spaced about a circumference of the peripheral peg in a first rotational orientation. The second radially extending feature has three lobes that are spaced about the circumference of the peripheral peg with a second rotational orientation that is angularly offset from the first rotational orientation.

According to some implementations of the present disclosure, a glenoid implant includes a body, a central peg, and a plurality of peripheral pegs. The body has a first side with a concave surface and a second opposing side with a convex surface. The convex surface is configured to engage a prepared glenoid of a patient. The convex surface has a peripheral area surrounding a central area. The central peg extends from the central area of the convex surface. The plurality of peripheral pegs extends from the peripheral area of the convex surface. Each of the plurality of peripheral pegs has at least a first set of resilient lobes at a first longitudinal position and a second set of resilient lobes at a second longitudinal position spaced from the first longitudinal position.

According to some implementations of the present disclosure, a glenoid implant includes a body, a central peg, and a plurality of peripheral pegs. The body has a first side with a concave surface and a second opposing side with a convex surface. The convex surface is configured to engage a prepared glenoid of a patient. The convex surface has a peripheral area surrounding a central area. The central peg extends from the central area of the convex surface. The plurality of peripheral pegs extends from the peripheral area of the convex surface. Each of the plurality of peripheral pegs has a plurality of radially extending features. Each of the plurality of radially extending features has three lobes that are spaced about a circumference of the respective one of the plurality of peripheral pegs. The three lobes of a first portion of the plurality of radially extending features have a first rotational orientation. The three lobes of a second portion of the plurality of radially extending features have a second rotational orientation that is angularly offset from the first rotational orientation. The three lobes of a third portion of the plurality of radially extending features have a third rotational orientation that is angularly offset from the first and the second rotational orientations.

According to some implementations of the present disclosure, a glenoid implant is provided that is to be coupled with a prepared glenoid of a patient. The prepared glenoid has a mating surface, a central bore, and a peripheral bore. The glenoid implant includes a body, a central peg, and a peripheral peg. The body has a concave surface configured to engage a humeral head implant component, and a convex surface configured to engage the mating surface of the prepared glenoid of the patient. The convex surface has a peripheral area surrounding a central area. The central peg extends from the central area of the convex surface. The central peg is configured to be affixed to the central bore of the prepared glenoid of the patient. The peripheral peg extends from the peripheral area of the convex surface. The peripheral peg has at least one radially extending feature. Responsive to at least a portion of the convex surface directly engaging the mating surface of the prepared glenoid, the at least one radially extending feature of the peripheral peg is configured to engage cancellous bone of the prepared glenoid and provide a sufficient amount of self-pressurization such that bone cement between the central peg and the central bore can cure with the at least a portion of the convex surface maintaining its direct engagement with the mating surface of the prepared glenoid without an external force being applied to the glenoid implant.

According to some implementations of the present disclosure, a method of making a glenoid implant includes providing a stock glenoid component. The stock glenoid component including a body, a central peg, and a peripheral peg. The body has a first side with a concave surface and a second opposing side with a convex surface. The convex surface has a peripheral area surrounding a central area. The central peg extends from the central area of the convex surface. The peripheral peg extends from the peripheral area of the convex surface. The peripheral peg has a generally cylindrical portion. The generally cylindrical portion of the peripheral peg is cut, via at least one of one or more tools, thereby creating a plurality of radially extending disks. The created plurality of radially extending disks is cut, via at least one of the one or more tools, in one or more helical patterns with respect to a central axis of the peripheral peg, thereby modifying each of the plurality of radially extending disks to have three lobes that are spaced about a circumference of the peripheral peg.

According to some implementations of the present disclosure, a method of installing a glenoid implant in a prepared glenoid of a patient is described. The prepared glenoid has a mating surface, a central bore, and a plurality of peripheral bores. The method includes providing a glenoid implant. The provided glenoid implant includes a body, a central peg, and a plurality of peripheral pegs. The body has a first side with a concave surface and a second opposing side with a convex surface. The convex surface has a peripheral area surrounding a central area. The central peg extends from the central area of the convex surface. The plurality of peripheral pegs extends from the peripheral area of the convex surface. Each of the peripheral pegs has at least one radially extending feature. Bone cement is applied to at least a portion of the central peg. The glenoid implant is positioned, via at least one of one or more tools, such that: (i) at least a portion of the convex surface directly engages the mating surface of the prepared glenoid, (ii) the central peg is positioned within the central bore of the prepared glenoid, and (iii) each of the plurality of peripheral pegs is positioned within a respective one of the peripheral bores of the prepared glenoid. The at least one of the one or more tools is disengaged from the glenoid implant prior to the bone cement applied to the at least a portion of the central peg curing. While the bone cement cures, the position of the glenoid implant is maintained relative to the prepared glenoid via the at least one radially extending feature of the plurality of peripheral pegs.

According to some implementations of the present disclosure, a shoulder implant system includes a humeral stem implant, a humeral neck implant component, a humeral head implant component, and a glenoid implant. The humeral stem implant has a fin that is coupled to an exterior surface thereof. The fin is inwardly tapered at an angle relative to vertical. At least a portion of the fin forms a wedge that directly engages and compacts cancellous bone during installation of the humeral stem implant. The humeral neck implant component is configured to be coupled with the humeral stem implant such that a portion of the humeral neck implant component protrudes from an angled face of the humeral stem implant. The humeral head implant component is configured to be coupled to the portion of the humeral neck implant component that protrudes from the angled face of the humeral stem implant. The glenoid implant has a concave surface configured to engage the humeral head implant component.

According to some implementations of the present disclosure, a shoulder implant system includes a humeral stem implant, a humeral neck implant component, a humeral head implant component, and a glenoid implant. The humeral stem implant has an interior bore. The humeral neck implant component is configured to be coupled with the humeral stem implant via the interior bore such that a portion of the humeral neck implant component protrudes from the humeral stem implant. The humeral head implant component is configured to be coupled to the portion of the humeral neck implant component that protrudes from the humeral stem implant. The glenoid implant has a body, a central peg, and a peripheral peg. The body has a first side with a concave surface and a second opposing side with a convex surface. The concave surface is configured to engage the humeral head implant component. The convex surface is configured to engage a prepared glenoid of a patient. The convex surface has a peripheral area surrounding a central area. The central peg extends from the central area of the convex surface and the peripheral peg extends from the peripheral area of the convex surface. The peripheral peg has a first set of resilient lobes at a first longitudinal position and a second set of resilient lobes at a second longitudinal position spaced from the first longitudinal position.

Additional aspects and implementations of the present disclosure will be apparent to those of ordinary skill in the art in view of the detailed description of various implementations, which is made with reference to the drawings, a brief description of which is provided below.

Figure 1A:
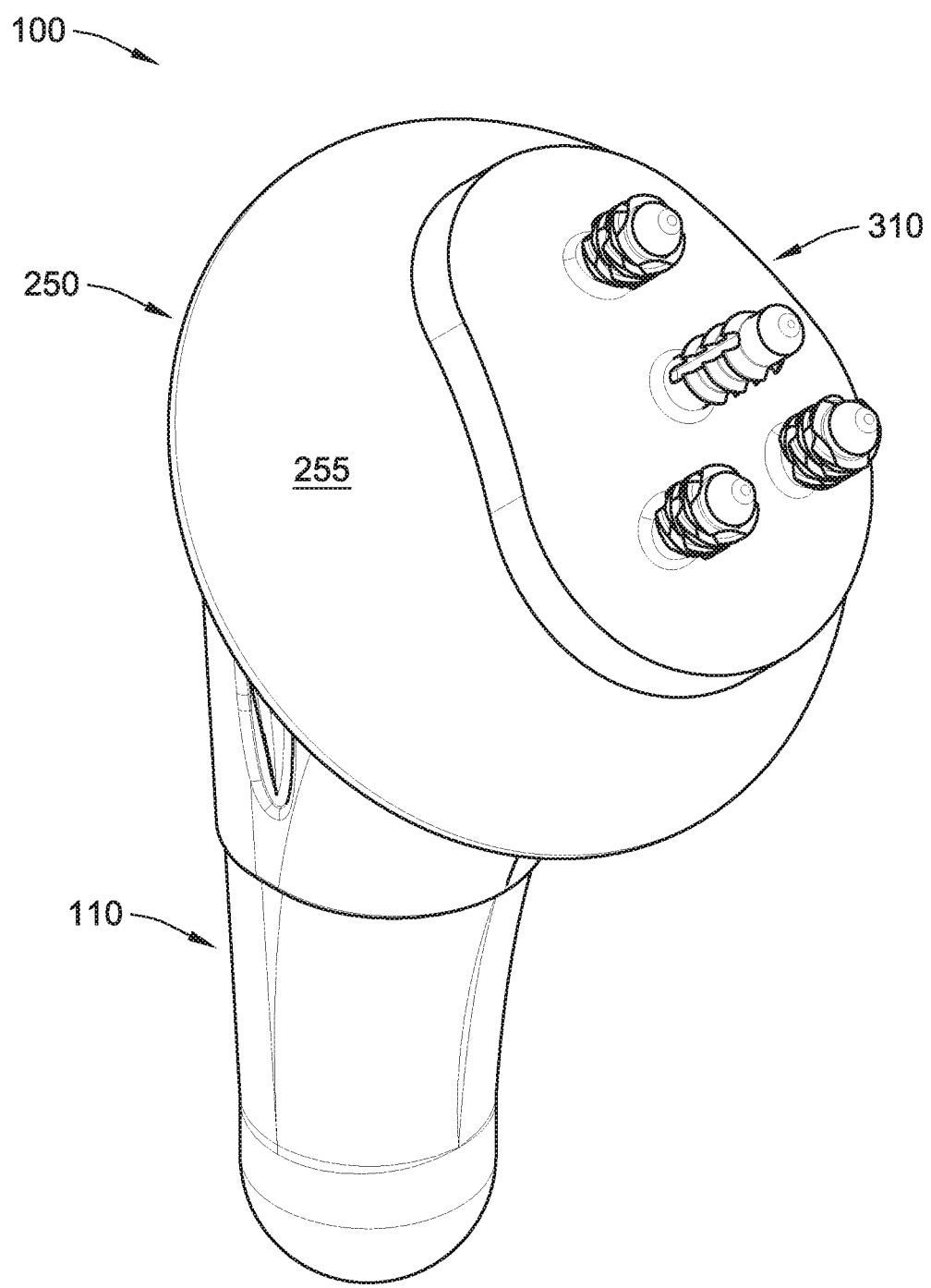
FIG. 1A is an assembled perspective view of a shoulder implant system according to some implementations of the present disclosure.

While the present disclosure is susceptible to various modifications and alternative forms, specific implementations have been shown by way of example in the drawings and will be described in detail herein. It should be understood, however, that the present disclosure is not intended to be limited to the particular forms disclosed. Rather, the present disclosure is intended to cover all modifications, equivalents, and alternatives falling within the spirit and scope of the present disclosure as defined by the appended claims.

DETAILED DESCRIPTION

While this disclosure is susceptible to embodiment in many different forms, there is shown in the drawings and will herein be described in detail preferred implementations of the disclosure with the understanding that the present disclosure is to be considered as an exemplification of the principles of the disclosure and is not intended to limit the broad aspect of the disclosure to the implementations illustrated.

Referring generally to FIGS. 1A-2B, a shoulder implant system 100 includes a humeral stem implant 110, a humeral neck implant component 210, a humeral head implant component 250, and a glenoid implant 310. Generally, the humeral stem implant 110 is installed/implanted in a prepared humerus bone of a patient such that a portion (e.g., a tapered face 132 shown in FIG. 7A) of the humeral stem implant 110 remains exposed to be coupled with a first end portion 212a (FIGS. 2A and 2B) of the humeral neck implant component 210. As such, a second opposing end portion 212b of the humeral neck implant component 210 is exposed and protruding such that the humeral head implant component 250 can be coupled thereto (best shown in FIG. 1B).

Figure 1B:
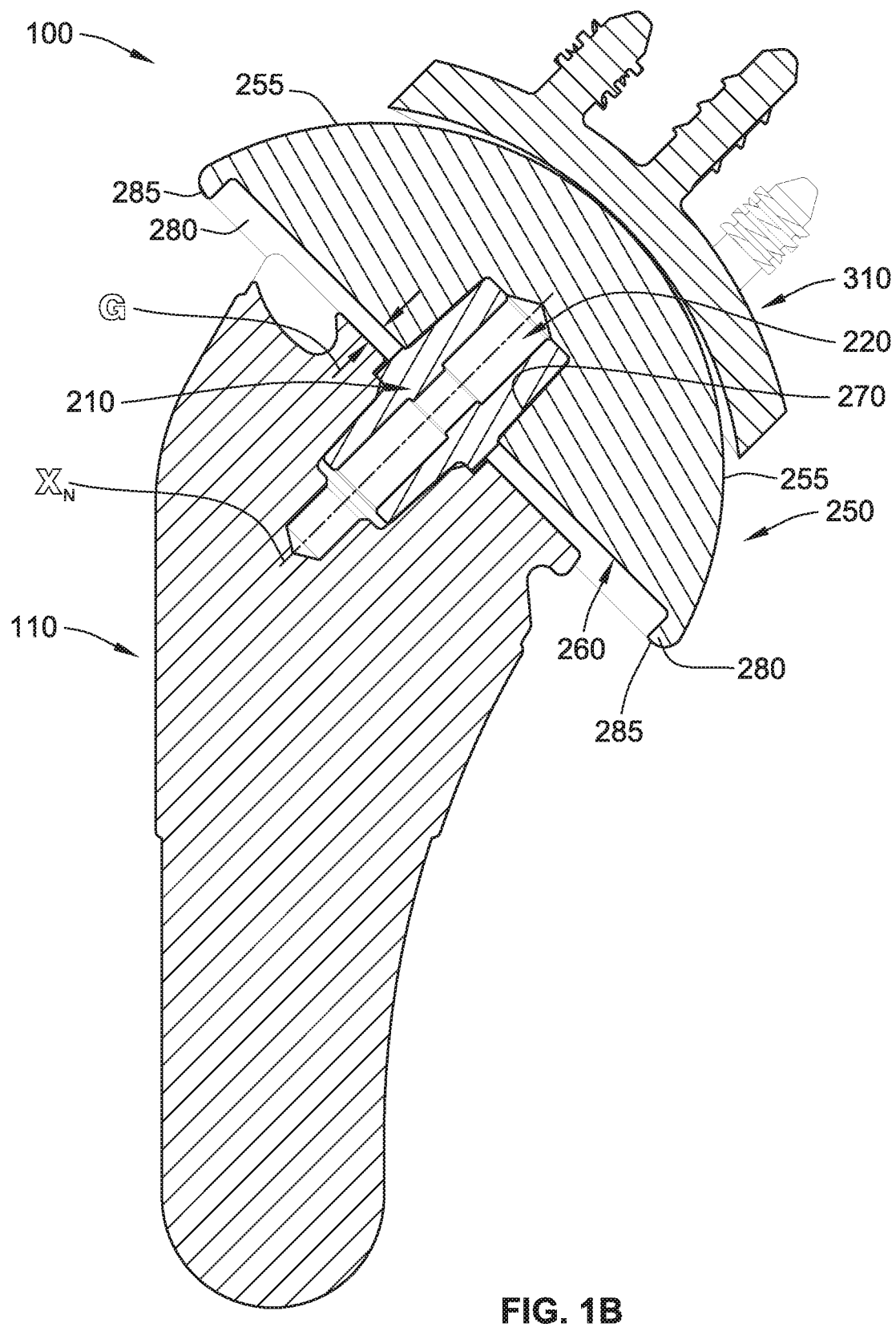
FIG. 1B is an assembled side cross-sectional view of the shoulder implant system of FIG. 1A.
Figure 2A:
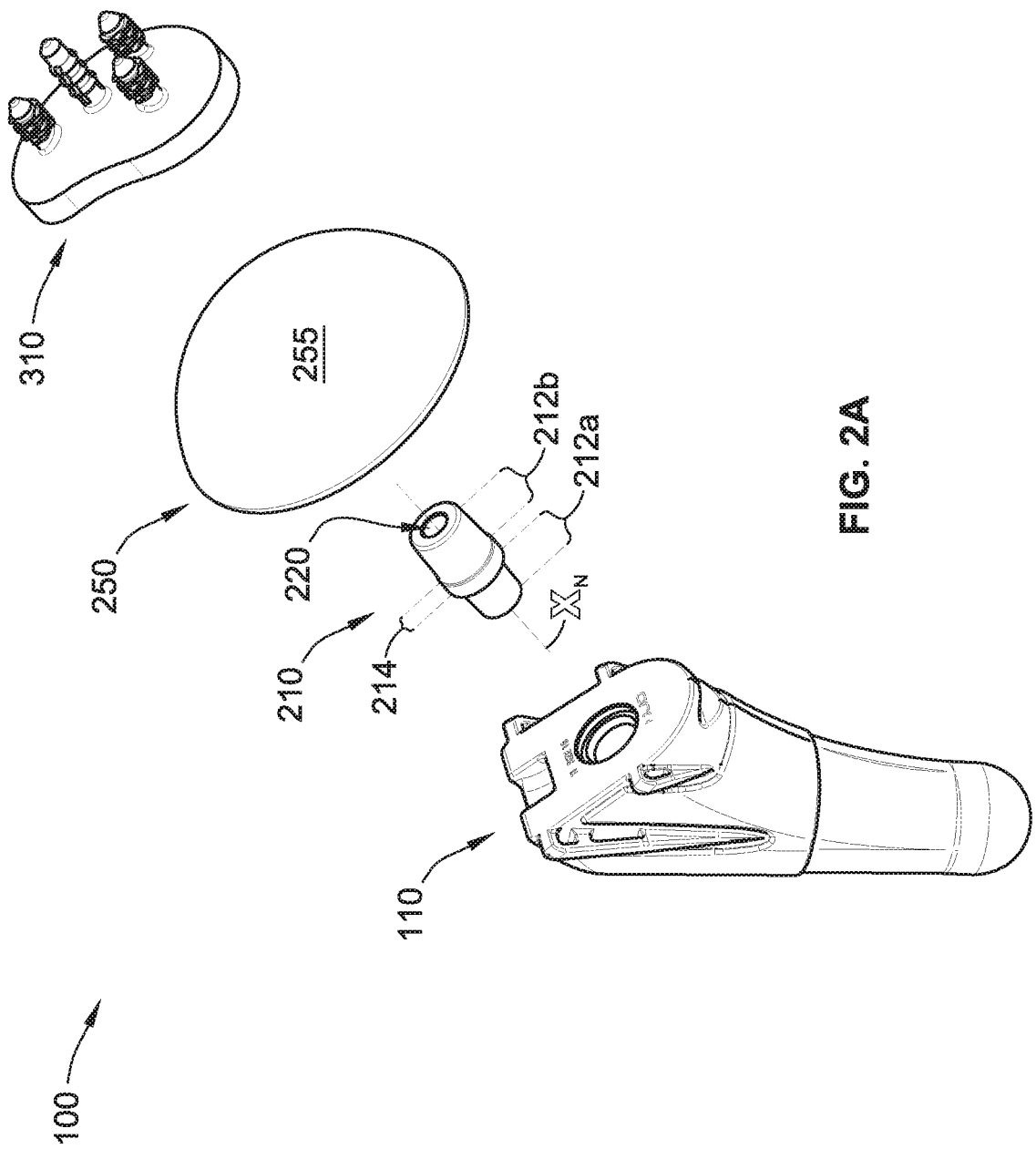
FIG. 2A is a first exploded perspective view of the shoulder implant system of FIG. 1A.
Figure 2B:
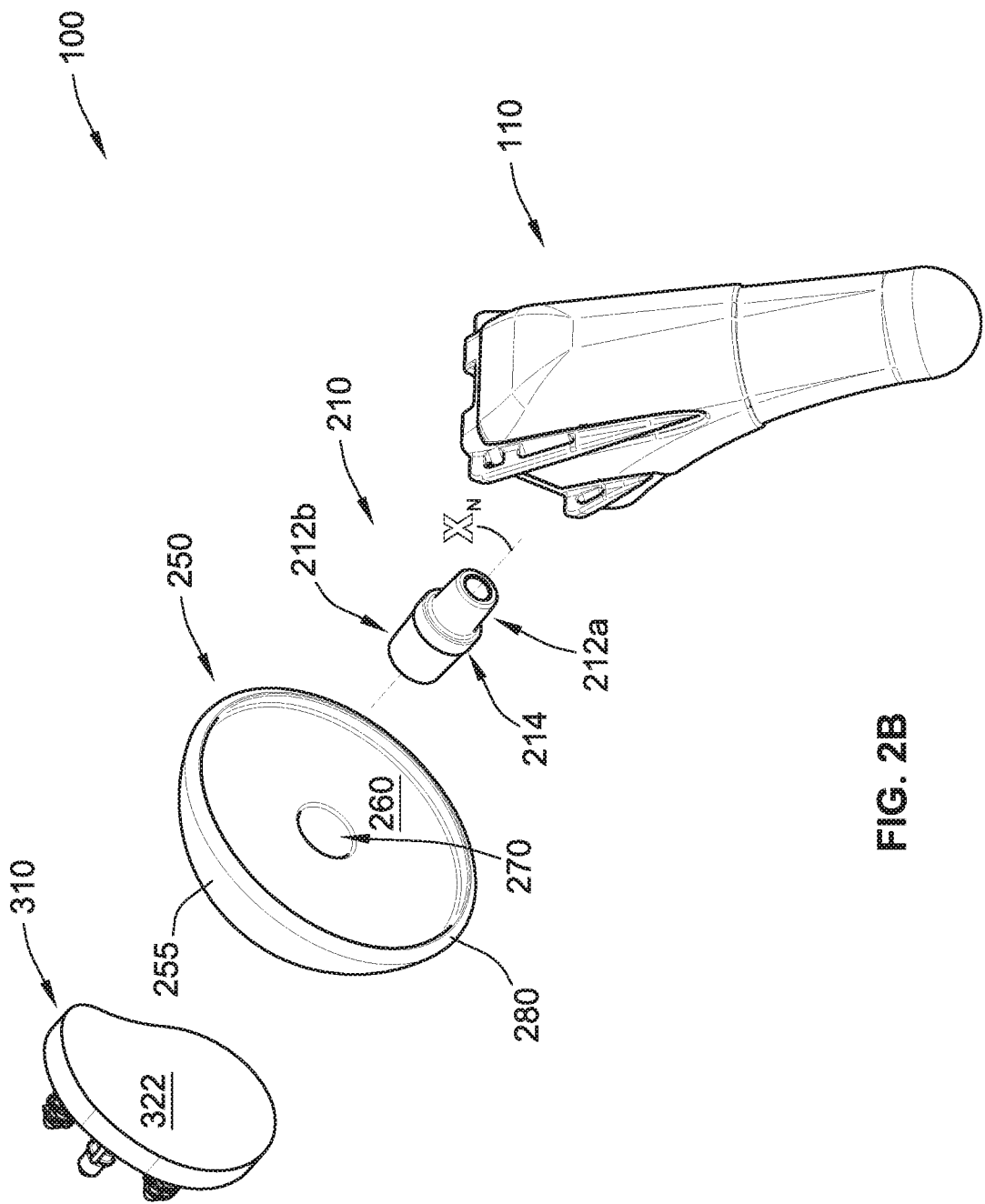
FIG. 2B is a second exploded perspective view of the shoulder implant system of FIG. 1A.

The humeral neck implant component 210 has the first end portion 212a, the second end portion 212b, a central portion 214, and a throughbore 220 (best shown in FIG. 1B). The first end portion 212a has a generally tapered cylindrical shape such that the humeral neck implant component 210 can mate with an interior bore 135 of the humeral stem implant 110 in a taper lock configuration (e.g., a morse taper lock). Specifically, the first end portion 212a tapers inwardly in a direction along a central axis $X_N$ of the humeral neck implant component 210 from the central portion 214 towards the first end portion 212a. Similarly, the second end portion 212b has a generally tapered cylindrical shape such that the humeral neck implant component 210 can mate with the humeral head implant component 250 in a taper lock configuration (e.g., a morse taper lock). Specifically, the second end portion 212b tapers inwardly in a direction along the central axis $X_N$ of the humeral neck implant component 210 from the central portion 214 towards the second end portion 212b.

As shown, the second end portion 212b has a relatively larger outer maximum diameter as compared with the first end portion 212a, although the reverse is contemplated. In some such implementations, the difference in outer maximum diameters of the first end portion 212a and second end portion 212b aids in the proper coupling of the humeral neck implant component 210 to the humeral stem implant 110 and the humeral head implant component 250.

The throughbore 220 of the humeral neck implant component 210 permits a tool to be positioned therethrough to aid in removing the humeral neck implant component 210 from an engagement (e.g., taper lock engagement) with the humeral stem implant 110. In some alternative implementations, the humeral neck implant component 210 does not include the throughbore 220.

While the humeral neck implant component 210 is shown as having a particular shape (i.e., generally cylindrical) and size, it is contemplated that the humeral neck implant component 210 can have a variety of other shapes and/or sizes. For example, the humeral neck implant component 210 can have a non-rotational shape, such as, for example, a generally rectangular cuboid shape, a generally clover shaped cross-section, a generally triangular shaped cross-section, etc., or any combination thereof.

The humeral head implant component 250 has a generally convex outer surface 255 (best shown in FIG. 2A), a generally flat inner surface 260 (best shown in FIG. 2B), an interior bore 270 (best shown in FIG. 2B), and an outer flange 280 (best shown in FIG. 1B). The generally convex outer surface 255 has a generally semi-spherical shape and is for engaging a corresponding concave surface 322 (FIG. 2B) of the glenoid implant 310 during operation of the shoulder implant system 100 in a patient.

The interior bore 270 of the humeral head implant component 250 is for engaging the second end portion 212b of the humeral neck implant component 210 in the taper lock configuration (e.g., a morse taper lock) as described above. As such, the interior bore 270 also tapers inwardly in the direction along the central axis $X_N$ of the humeral neck implant component 210 from the central portion 214 towards the second end portion 212b, as shown in FIG. 1B.

The generally flat inner surface 260 is set back from (i.e., recessed) an edge 285 (FIG. 1B) of the outer flange 280 such that the generally flat inner surface 260 does not directly engage or otherwise touch the humeral stem implant 110 (i) during installation of the humeral head implant component 250 onto the humeral neck implant component 210, which could impede the taper lock from securing therebetween and/or (ii) when the humeral head implant component 250 is fully engaged with or fully seated on the humeral neck implant component 210. In some such implementations, the interior bore 270 of the humeral head implant component 250 and the second end portion 212b of the humeral neck implant component 210 are configured such that a gap, G, is maintained between the generally flat inner surface 260 and the tapered face 132 (FIG. 7A) of the humeral stem implant 110. The gap, G, can be, for example, between about half of a millimeter and about three millimeters, between about half of a millimeter and about two millimeters, between about half of a millimeter and about one millimeter, about one millimeter, etc. In some implementations, the gap, G, also provides a space such that the humeral head implant component 250 can move (e.g., flex, tilt, etc.) relative to the humeral stem implant 110 when installed in a patient.

Figure 3:
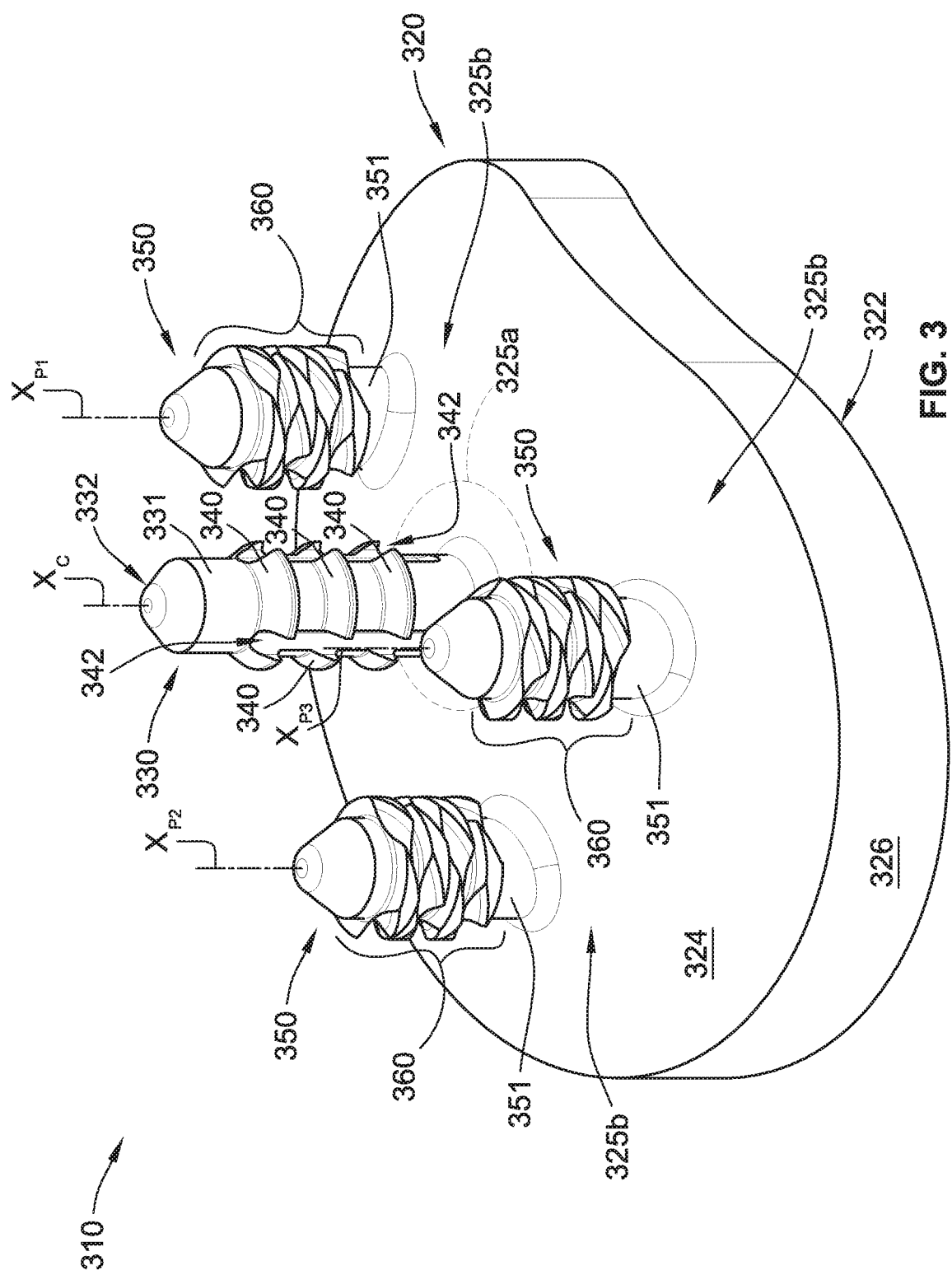
FIG. 3 is a perspective view of a glenoid implant of the shoulder implant system of FIG. 1A according to some implementations of the present disclosure.
Figure 4A:
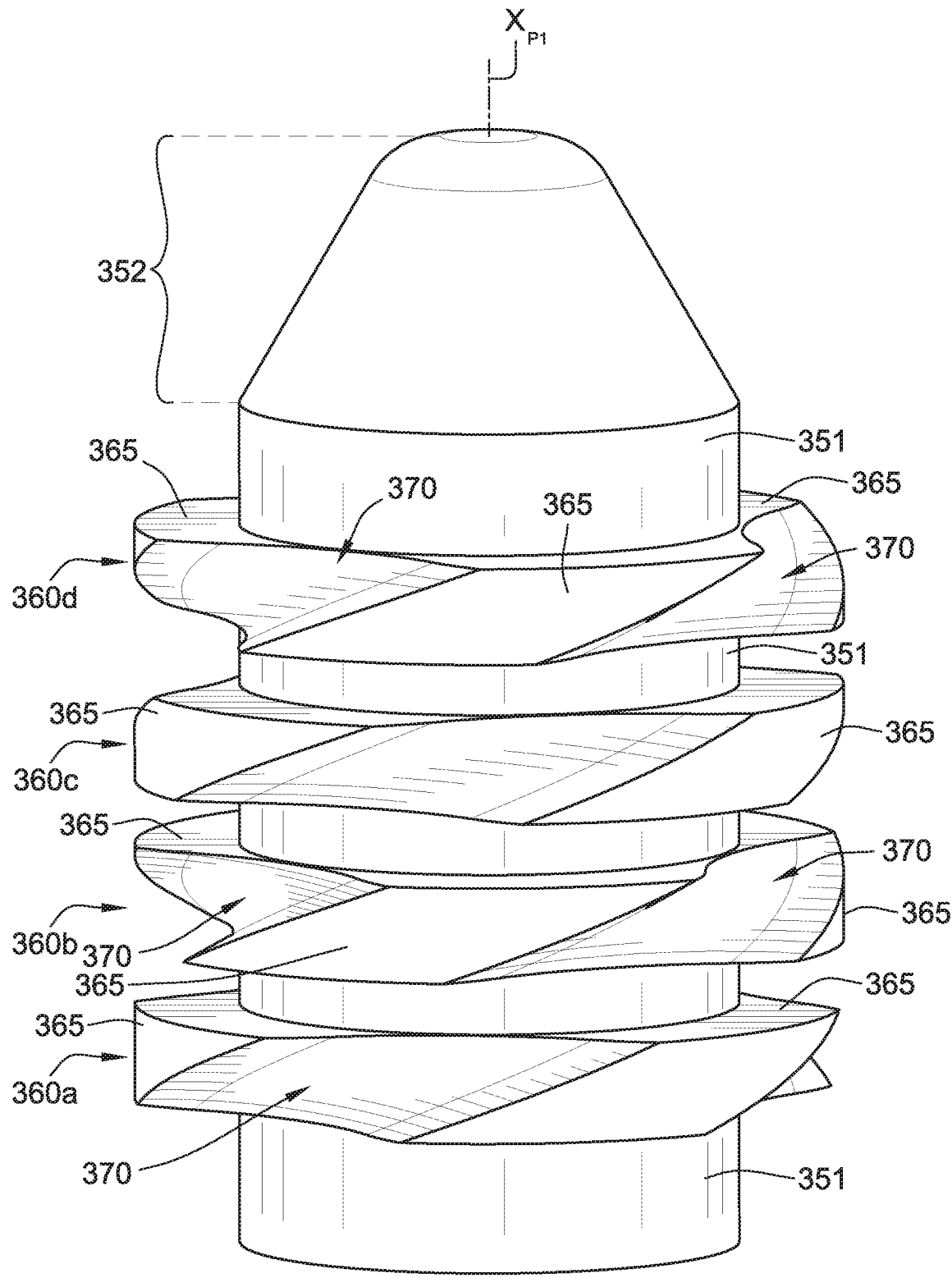
FIG. 4A is a partial perspective view of a peripheral peg of the glenoid implant of FIG. 3.
Figure 4B:
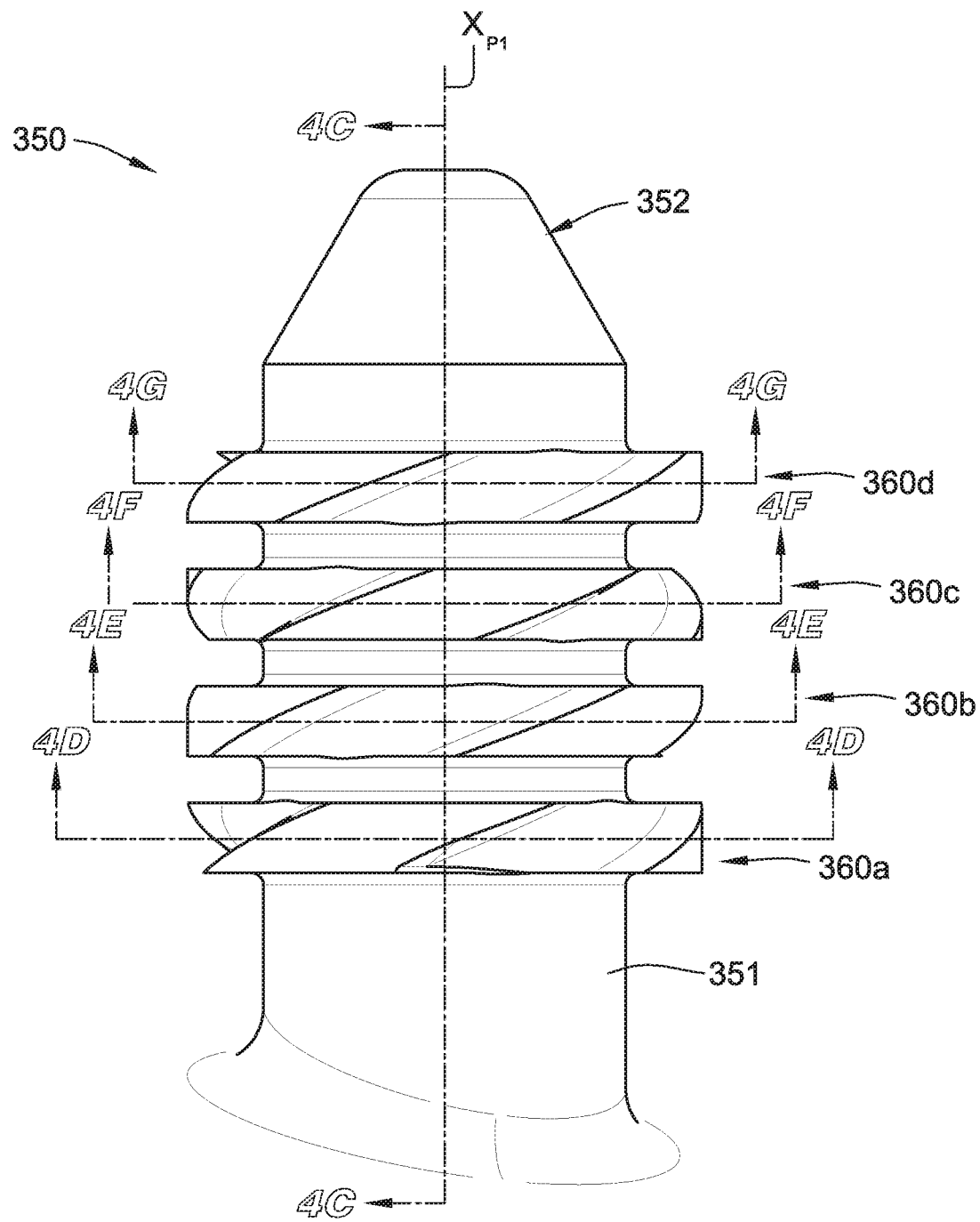
FIG. 4B is a plan view of the peripheral peg of FIG. 4A.
Figure 4E:
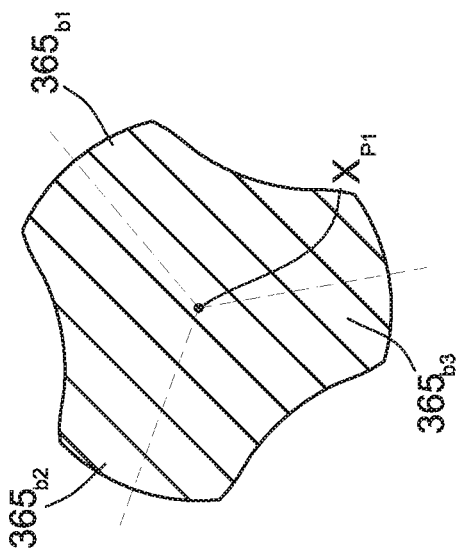
FIG. 4E is a cross-sectional view of the peripheral peg of FIG. 4B taken at line 4E-4E.
Figure 4D:
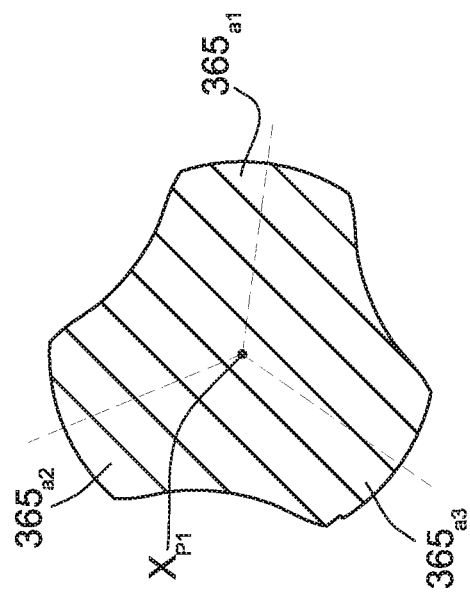
FIG. 4D is a cross-sectional view of the peripheral peg of FIG. 4B taken at line 4D-4D.
Figure 4G:
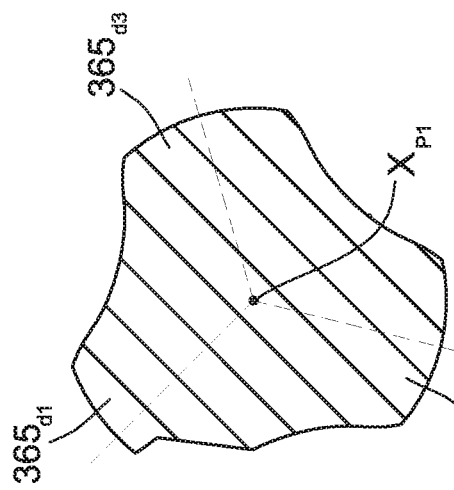
FIG. 4G is a cross-sectional view of the peripheral peg of FIG. 4B taken at line 4G-4G.

Generally referring to FIGS. 3-4G, the glenoid implant 310 includes a body 320, a central peg 330, and three peripheral pegs 350 (although any number of peripheral pegs is contemplated, such as, for example, one peripheral peg, two peripheral pegs, four peripheral pegs, five peripheral pegs, etc.). The body 320 of the glenoid implant 310 has an irregular shape that generally corresponds to the shape of the natural glenoid cavity or natural glenoid fossa of the scapula of a patient. In some implementations, the cross-sectional shape of the body 320 is generally egg shaped.

The body 320 has a laterally facing concave surface 322 (best shown in FIG. 2B) for engaging the humeral head implant component 250. The body 320 also has a medially facing convex surface 324 (best shown in FIG. 3) for engaging a mating surface of a prepared glenoid of a patient (e.g., a shaved and/or drilled glenoid cavity of the patient). The convex surface 324 generally has a peripheral area 325b surrounding a central area 325a. The central area 325a includes the geometric center of the convex surface 324 and a portion of the convex surface 324 surrounding the geometric center. In some implementations, the central area 325a includes between about five percent and about thirty percent of the total surface area of the convex surface 324 and the peripheral area 325b is the balance. In some implementations, the central area 325a includes between about ten percent and about twenty-five percent of the total surface area of the convex surface 324 and the peripheral area 325b is the balance. In some implementations, the central area 325a includes between about fifteen percent and about twenty percent of the total surface area of the convex surface 324 and the peripheral area 325b is the balance. The central area 325a is shown as being a generally circular area about the central peg 330, although the central area 325a can have any shape (e.g., oval, square, triangle, polygon, etc., or any combination thereof). The body 320 of the glenoid implant 310 also has an edge surface 326 that extends between the concave surface 322 and the convex surface 324. The edge surface 326 varies based on the thickness of the body 320.

The glenoid implant 310 is a single monolithic part. In some implementations, the glenoid implant 310 is milled from a solid block of material. In some other implementations, the glenoid implant 310 is made by a 3D printer that prints the glenoid implant 310 as a single monolithic part. Alternatively, the glenoid implant 310 is not monolithic. In some such alternative implementations, the body 320 of the glenoid implant 310 is a first component that is attached to the central peg 330 and the peripheral pegs 350, which are separate components, respectively. The glenoid implant 310 can be made from any material, such as, for example, plastic (e.g., polyethylene, high density polyethylene, ultra high density polyethylene, etc.), metal (e.g., stainless steel, nickel, titanium, etc.), ceramic, or any combination thereof.

The central peg 330 has a central axis $X_C$ (FIG. 3) and each of the three peripheral pegs 350 has a respective central axis $X_{P1}$, $X_{P2}$, and $X_{P3}$ (FIG. 3). The central axis $X_C$ is generally parallel to each of the central axes $X_{P1}$, $X_{P2}$, and $X_{P3}$, such that the glenoid implant 310 can be installed in a single medial direction causing the central peg 330 and the three peripheral pegs 350 to enter and engage respective bores drilled into the prepared glenoid of the patient at about the same time (e.g., the central peg 330 enters first due to its relatively larger height/length).

The central peg 330 has a cylindrically shaped body 331. The cylindrically shaped body 331 has a first end that is integral with the body 320 of the glenoid implant 310 and a second opposing end that forms a rounded and/or tapered tip portion 332 of the central peg 330. The tip portion 332 of the central peg 330 aids the central peg 330 in engaging and entering a central bore (not shown) in the prepared glenoid during the installation of the glenoid implant 330.

The central peg 330 has a multitude of fins 340 extending from the cylindrically shaped body 331 of the central peg 330. The fins 340 are rigid and do not bend or deflect or deform or otherwise move relative to the cylindrically shaped body 331 when the glenoid implant 310 is installed (e.g., causing the central peg 330 to be positioned in the central bore of the prepared glenoid of the patient). The fins 340 are spaced along a length/height of the cylindrically shaped body 331 and about a circumference of the cylindrically shaped body 331 such that one or more channels 342 (e.g., two vertical channels, three vertical channels, etc.) are formed between the fins 340. The fins 340 and the channels 342 provide surfaces, grooves, and/or undercuts for engaging and/or holding bone cement (not shown) for use in securing the central peg 330 to the central bore of the prepared glenoid of the patient.

In some implementations, the central bore of the prepared glenoid has an internal diameter that is larger than a maximum outer diameter of the central peg 330 (including the fins 340). As such, a relatively larger bone cement mantle can be formed to aid in rigidly coupling the central peg 330 to the central bore of the prepared glenoid of the patient. In some alternative implementations, the central bore of the prepared glenoid has an internal diameter that is about equal to or slightly smaller than the maximum outer diameter of the central peg 330 (including the fins 340). In some such alternative implementations, the fins 340 are engaged and slightly compressed by the central bore, but the fins 340 generally do not bend or deflect or deform or otherwise move relative to the cylindrically shaped body 331.

The central peg 330 has a height/length and the maximum outer diameter. In some implementations, the height of the central peg 330 is between about five millimeters and about thirty millimeters. In some other implementations, the height of the central peg 330 is between about ten millimeters and about twenty-five millimeters. In some implementations, the height of the central peg 330 is about fifteen millimeters. In some implementations, the maximum outer diameter of the central peg 330 (including the fins 340) is between about one millimeter and about eight millimeters. In some other implementations, the maximum outer diameter of the central peg 330 is between about two millimeters and about six millimeters. In some other implementations, the maximum outer diameter of the central peg 330 is between about three millimeters and about five millimeters.

Similarly to the central peg 330, each of the peripheral pegs 350 has a cylindrically shaped body 351. The cylindrically shaped body 351 has a first end that is integral with the body 320 of the glenoid implant 310 and a second opposing end that forms a rounded and/or tapered tip portion 352 (best shown in FIG. 4A) of the peripheral peg 350. The tip portion 352 of the peripheral peg 350 aids the peripheral peg 350 in engaging and entering a respective peripheral bore (not shown) in the prepared glenoid during the installation of the glenoid implant 330.

Each of the peripheral pegs 350 has a multitude of radially extending features 360 (FIG. 3) extending from the cylindrically shaped body 351 of the peripheral peg 350. As best shown in FIG. 4A, each of the peripheral pegs 350 has four radially extending features 360a-d extending from the cylindrically shaped body 351, although, each of the peripheral pegs 350 can have any number of radially extending features 360 (e.g., one radially extending feature, two radially extending features, three radially extending features, five radially extending features, etc.). The four radially extending features 360 are positioned at four longitudinal positions of the cylindrically shaped body 351 of the peripheral peg 350.

Specifically, as shown in FIG. 4A, a first one of the radially extending features 360a is positioned at a first longitudinal position of the peripheral peg 350 that is closest to the convex surface 324 (FIG. 3) of the body 320 of the glenoid implant 310. A second one of the radially extending features 360b is positioned at a second longitudinal position of the peripheral peg 350 that is directly adjacent to and more distal than the first radially extending feature 360a. A third one of the radially extending features 360c is positioned at a third longitudinal position of the peripheral peg 350 that is directly adjacent to the second radially extending feature 360b and more distal than the first and the second radially extending features 360a, 360b. A fourth one of the radially extending features 360d is positioned at a fourth longitudinal position of the peripheral peg 350 that is directly adjacent to the third radially extending feature 360c and more distal than the first, the second, and the third radially extending features 360a, 360b, 360c. Further, the radially extending features 360a-d are separated from one another along the cylindrically shaped body 351 of the peripheral peg 350 such that a portion of the cylindrically shaped body 351 is exposed between the radially extending features 360a-d. As such, the radially extending features 360 have clearance to bend and or deflect.

Figure 5A:
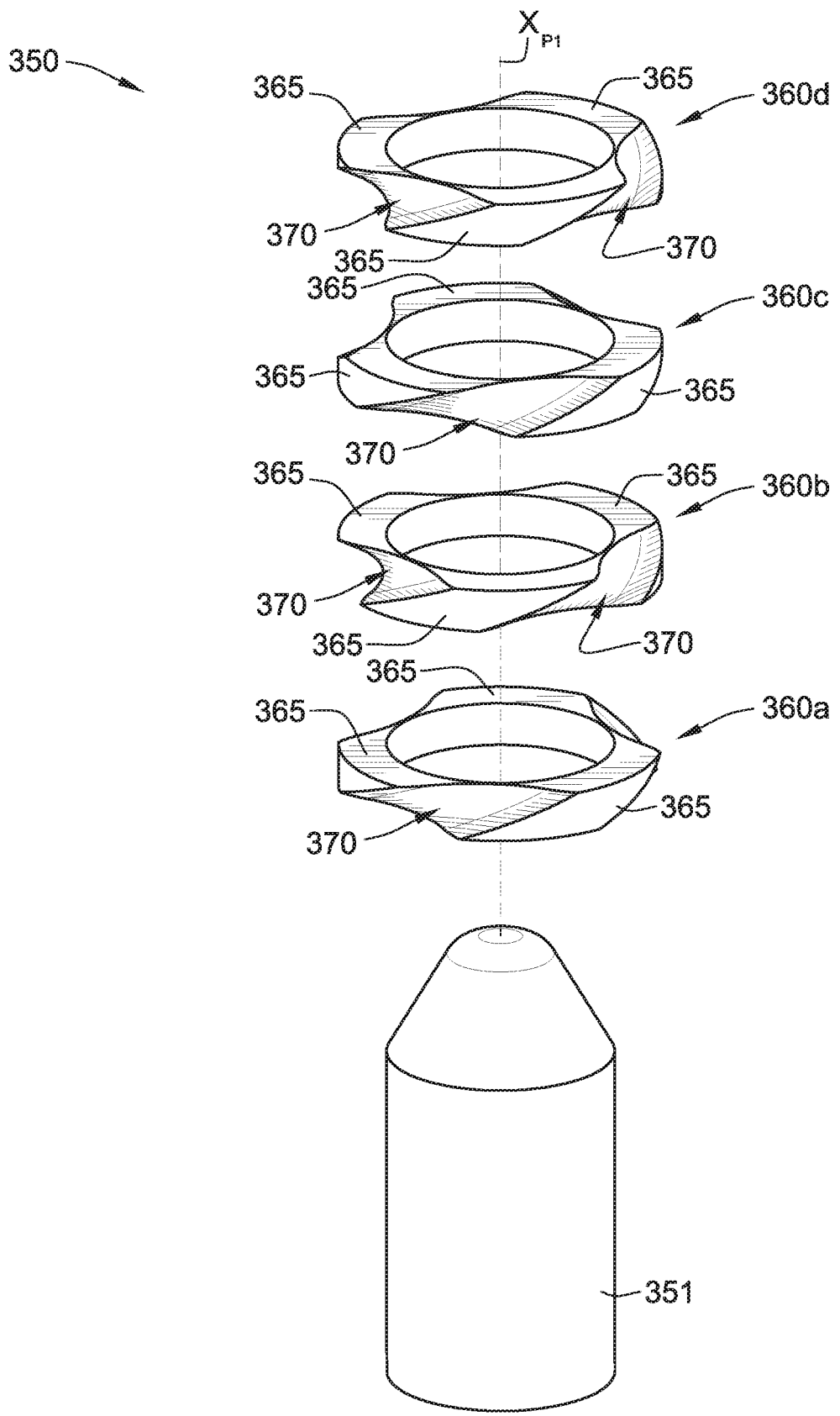
FIG. 5A is a perspective view of the peripheral peg of FIG. 4A with a plurality of radially extending features exploded therefrom to better illustrate the radially extending features according to some implementations of the present disclosure.

Each of the radially extending features 360 has a multitude of lobes 365. As best shown in FIG. 5A, which is for illustrative purposes showing the radially extending features 360a-d exploded from the cylindrically shaped body 351, each of the radially extending features 360a-d has three lobes 365 spaced about a circumference of the cylindrically shaped body 351. Each of the lobes 365 is deflectable and flexible and resilient such that each lobe 365 bends or deflects relative to the cylindrically shaped body 351 when the glenoid implant 310 is installed (e.g., when the peripheral pegs 350 are positioned in their respective peripheral bores of the prepared glenoid of the patient). In some such implementations, each of the lobes 365 deflects and/or deforms when engaged by cortical bone of the prepared glenoid of the patient during installation.

Figure 5B:
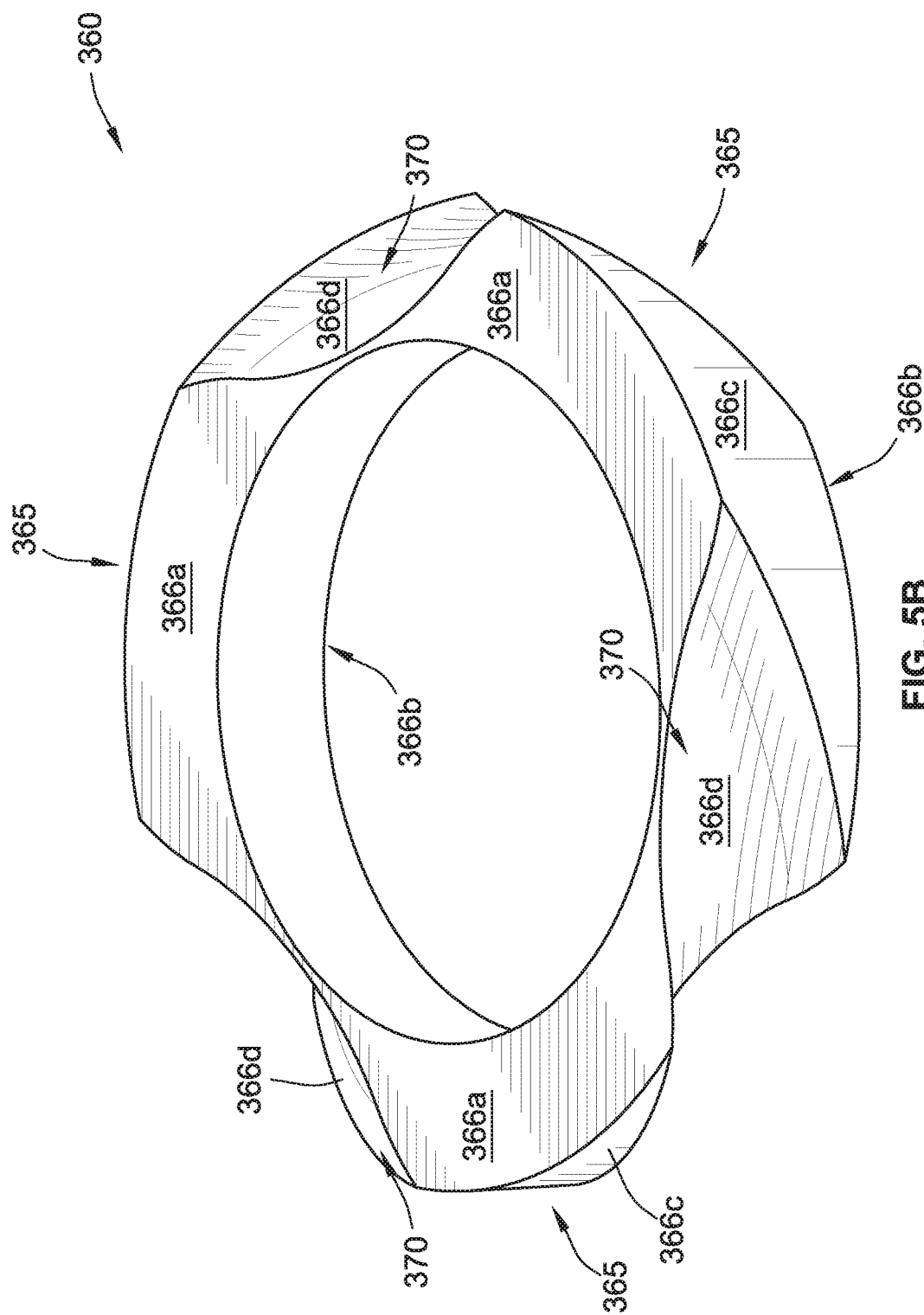
FIG. 5B is an enlarged perspective view of one of the plurality of radially extending features of FIG. 5A.

The lobes 365 are spaced about the circumference of the cylindrically shaped body 351 such that one or more channels 370 are formed between the lobes 365. As best shown in FIGS. 4A and 5A-5B, the one or more channels 370 includes three channels, where each of the three channels 370 has a generally helical path about the central axis $X_{P1}$ of the peripheral peg 350. Further, the lobes 365 of each radially extending feature 360 are angularly offset from the lobes 365 of each directly adjacent radially extending feature 360, which contributes to the generally helical shape of the channels 370.

Figure 4F:
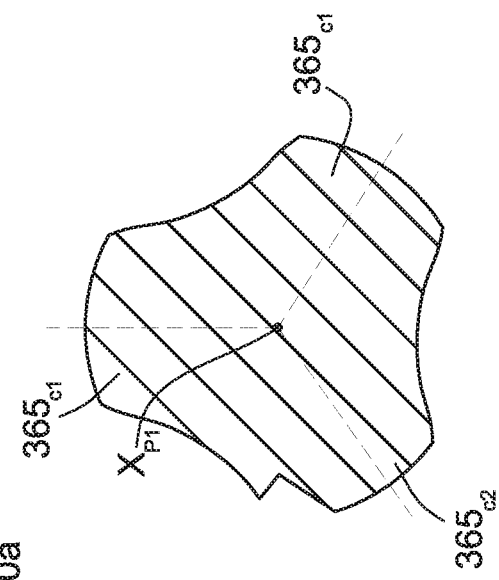
FIG. 4F is a cross-sectional view of the peripheral peg of FIG. 4B taken at line 4F-4F.
Figure 4C:
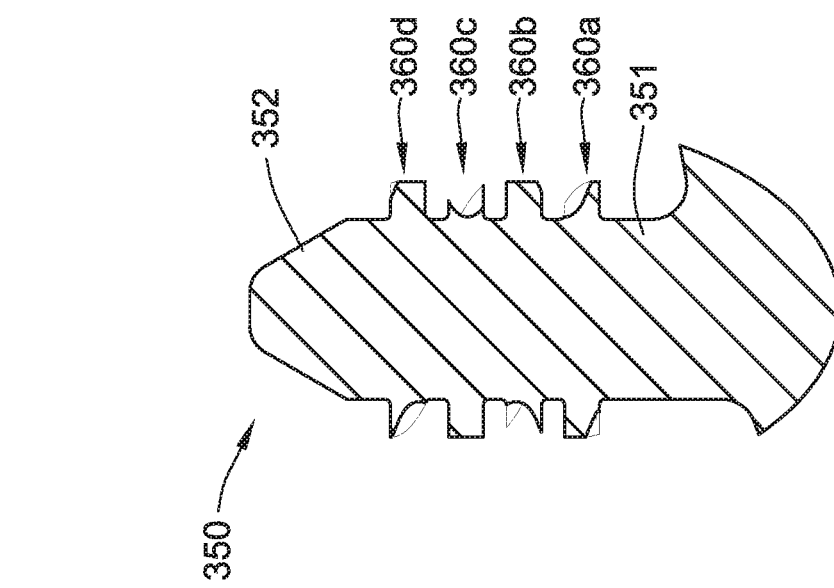
FIG. 4C is a cross-sectional view of the peripheral peg of FIG. 4B taken at line 4C-4C.

As best shown in FIGS. 4D-4G, which are cross-sectional views through each of the four radially extending features 360a-d shown in FIG. 4B, the first radially extending feature 360a (FIG. 4D) has three lobes $365a_1$, $365a_2$, and $365a_3$, that have a first rotational orientation about the central axis $X_{P1}$. The second radially extending feature 360b (FIG. 4E) has three lobes $365b_1$, $365b_2$, and $365b_3$, that have a second rotational orientation about the central axis $X_{P1}$, where the second rotational orientation (FIG. 4E) is angularly offset from the first rotational orientation (FIG. 4D). The third radially extending feature 360c (FIG. 4F) has three lobes $365c_1$, $365c_2$, and $365c_3$, that have a third rotational orientation about the central axis $X_{P1}$, where the third rotational orientation (FIG. 4F) is angularly offset from the first rotational orientation (FIG. 4D) and from the second rotational orientation (FIG. 4E). The fourth radially extending feature 360d (FIG. 4G) has three lobes $365d_1$, $365d_2$, and $365d_3$, that have a fourth rotational orientation about the central axis $X_{P1}$, where the fourth rotational orientation (FIG. 4G) is angularly offset from the first rotational orientation (FIG. 4D), from the second rotational orientation (FIG. 4E), and from the third rotational orientation (FIG. 4F). The rotational orientations are highlighted/illustrated for each of the radially extending feature 360a-d with three dashed lines that extend from a center point through the middle of each of the respective three lobes.

Referring to FIG. 5B, an enlarged view of one of the radially extending features 360 is shown exploded from the cylindrically shaped body 351 to better illustrate the radially extending features 360 and the lobes 365. As shown, each of the lobes 365 has an upper surface 366a, an opposing lower surface 366b, an outer edge surface 366c, and shared side surfaces 366d. The shared side surfaces 366d are shared between two directly adjacent ones of the lobes 365. Further, the shared side surfaces 366d are defined by the helical channels 370.

The lobes 360 and the helical channels 370 provide surfaces, grooves, and/or undercuts for engaging and/or holding bone cement (not shown) for use in securing the peripheral pegs 350 to the peripheral bores (not shown) in the prepared glenoid of the patient. In some implementations, the peripheral pegs 350 are not secured to the peripheral bores with bone cement. Rather, in some such implementations, the radially extending features 360 engage cancellous bone of the prepared glenoid and provide a sufficient amount of retention and/or pressurization such that bone cement is not needed between the peripheral pegs 350 and the peripheral bores in the prepared glenoid of the patient.

As best shown in FIG. 3, each of the peripheral pegs 350 has a height/length and a maximum outer diameter. The height of each of the peripheral pegs 350 is less than the height of the central peg 330. In some implementations, the height of each of the peripheral pegs 350 is less than seventy-five percent of the height of the central peg 330. In some implementations, the height of each of the peripheral pegs 350 is less than sixty percent of the height of the central peg 330. In some implementations, the height of each of the peripheral pegs 350 is less than fifty percent of the height of the central peg 330. In some implementations, the height of each of the peripheral pegs 350 is between two millimeters and about twenty millimeters. In some other implementations, the height of each of the peripheral pegs 350 is between five millimeters and about fifteen millimeters. In some implementations, the height of each of the peripheral pegs 350 is about eight millimeters.

In some implementations, the maximum outer diameter of each of the peripheral pegs 350 (including the radially extending features 360) is greater than the maximum outer diameter of the central peg 330 (including the fins 340) (e.g., five percent greater, ten percent greater, fifteen percent greater, twenty percent greater, thirty percent greater, fifty percent greater, etc.). In some implementations, the maximum outer diameter of each of the peripheral pegs 350 (including the radially extending features 360) is between about one millimeter and about fifteen millimeters. In some other implementations, the maximum outer diameter of each of the peripheral pegs 350 (including the radially extending features 360) is between about three millimeters and about eight millimeters. In some other implementations, the maximum outer diameter of each of the peripheral pegs 350 (including the radially extending features 360) is between about four millimeters and about six millimeters. In some implementations, the outer diameter of the cylindrically shaped body 351 of each of the peripheral pegs 350 is greater than the outer diameter of the cylindrically shaped body 331 of the central peg 330 (e.g., five percent greater, ten percent greater, fifteen percent greater, twenty percent greater, thirty percent greater, fifty percent greater, etc.).

A method of installing the glenoid implant 310 of the present disclosure into a prepared glenoid of a patient is now described. Initially, the natural glenoid of the patient is prepared using techniques and/or tools to shave the natural glenoid such that a mating surface or an exterior surface of the natural glenoid generally corresponds with the convex surface 324 of the glenoid implant 310. The preparation further includes drilling a central bore in the natural glenoid that receives the central peg 330. The preparation further includes, using, for example, a drill guide, to drill a set of peripheral bores in the natural glenoid that receive respective ones of the three peripheral pegs 350. With the natural glenoid so prepared, the glenoid implant 310 is ready to be installed.

Bone cement is applied to at least a portion of the central peg 330. Bone cement can also be applied to at least a portion of the convex surface 324, but in some implementations, bone cement is not applied to the convex surface 324. Further, bone cement can also be applied to at least a portion of one or more of the peripheral pegs 350, but in some implementations, bone cement is not applied to any of the peripheral pegs 350.

With the bone cement applied to the at least a portion of the central peg 330, using a tool to hold the glenoid implant 310, the glenoid implant 310 is fully installed/seated against the prepared glenoid where the glenoid implant is positioned such that (1) at least a portion of the convex surface 324 directly engages the mating surface of the prepared glenoid, (2) the central peg 330 is positioned within the central bore of the prepared glenoid, and (3) each of the three of peripheral pegs 350 is positioned within a respective one of the peripheral bores of the prepared glenoid. During this installation, the tip portion 332 of the central peg 330 first engages and enters the central bore of the prepared glenoid. Then the tip portions 352 of each of the peripheral pegs 350 engage and enter their respective peripheral bores of the prepared glenoid. As the peripheral pegs 350 are moved into the peripheral bores, the lobes 365 of at least a portion of the radially extending features 360 are directly engaged by cortical bone of the prepared glenoid, which causes the lobes 365 to deflect and/or bend relative to the cylindrically shaped body 351 of the respective peripheral peg 350. In some such implementations, the lobes 365 also deform (e.g., plastic deformation) and take a hook and/or barb shape that engages the cancellous bone of the prepared glenoid when the glenoid implant 310 is fully installed (e.g., when all of or a majority portion of the convex surface 324 directly engages the mating surface of the prepared glenoid).

With the glenoid implant 310 fully installed/seated, the tool holding the glenoid implant 310 is disengaged therefrom prior to the bone cement between the central peg 330 and the central bore having an opportunity to cure (e.g., harden). The fully installed/seated position of the glenoid implant 310 relative to the prepared glenoid is, however, maintained without use of the tool or any other tool, by way of the radially extending features 360 of the three of peripheral pegs 350, which engage the cancellous bone of the prepared glenoid and provide a sufficient amount of self-pressurization such that (1) the bone cement between the central peg 330 and the central bore of the prepared glenoid can cure without an external force holding the glenoid implant 310 in position, (2) the bone cement, if applied thereto, between the at least a portion of the convex surface 324 and the mating surface of the prepared glenoid can cure without an external force holding the glenoid implant 310 in position, and (3) the bone cement, if applied thereto, between the at least a portion of the one or more of the peripheral pegs 350 and the respective peripheral bores of the prepared glenoid can cure without an external force holding the glenoid implant 310 in position.

Figure 6B:
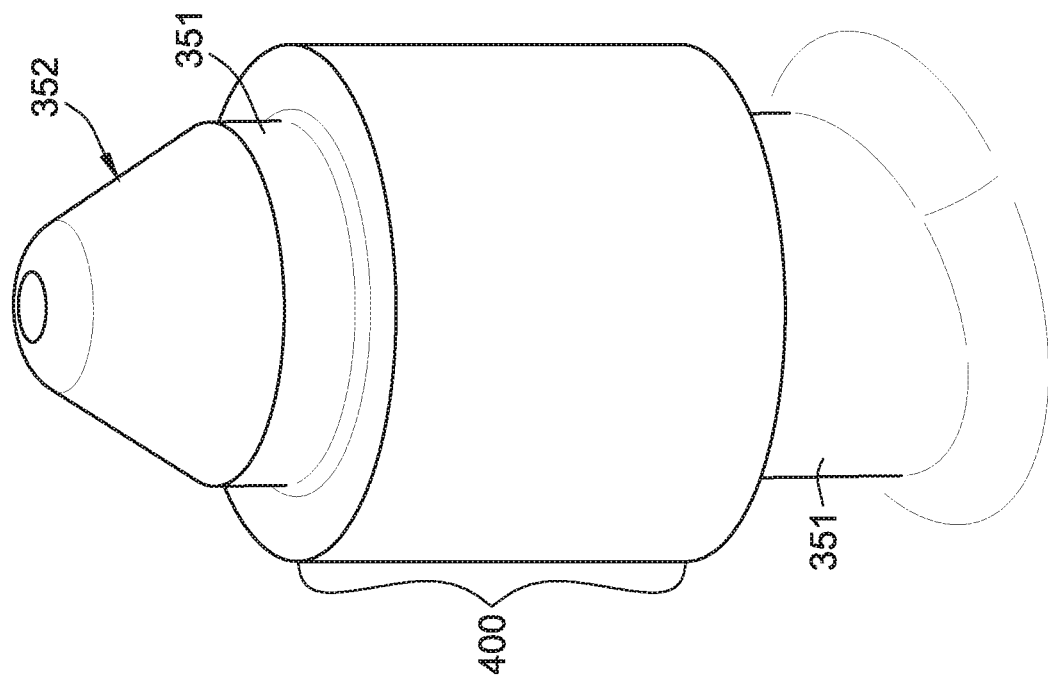
FIG. 6B is a perspective view of a partially formed version of the peripheral peg of FIG. 6A.
Figure 6A:
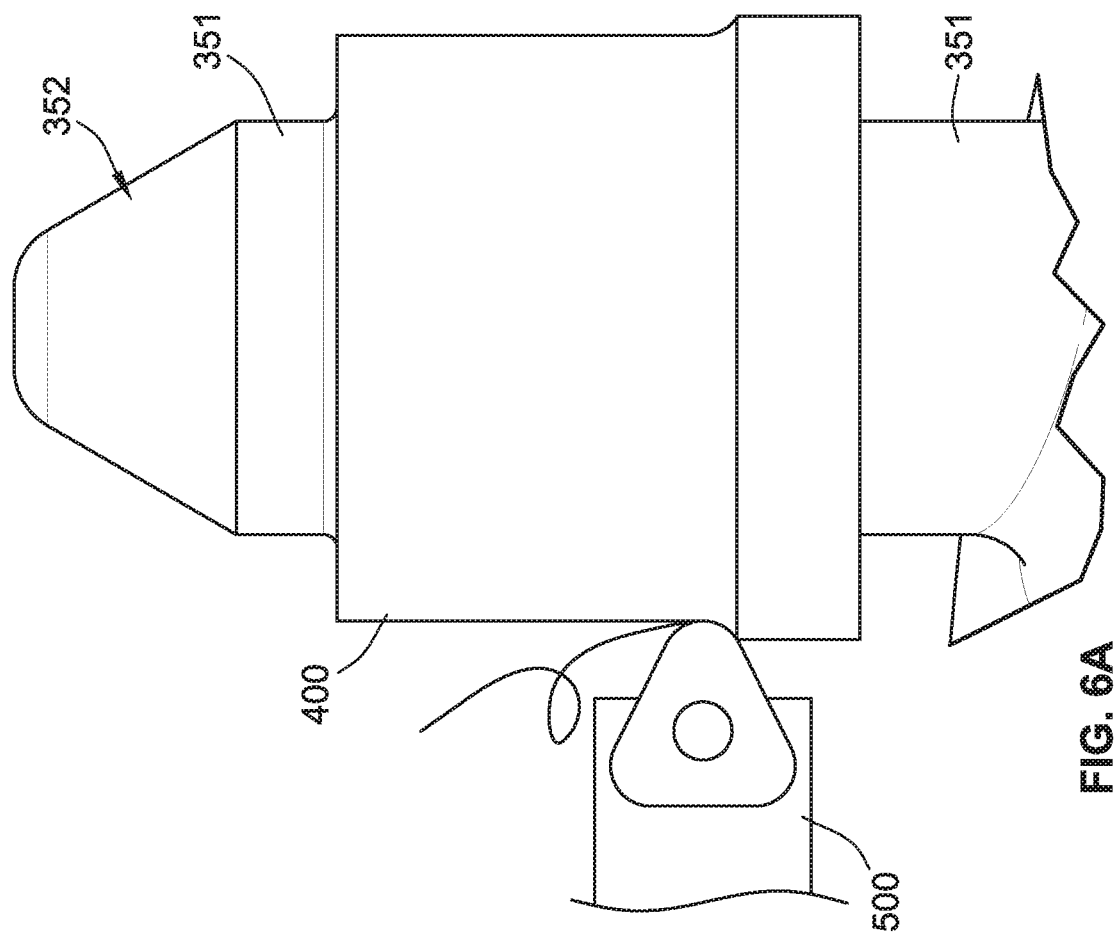
FIG. 6A is a side view illustrating a tool starting to form a peripheral peg according to some implementations of the present disclosure.

Generally referring to FIGS. 6A-H, a method of making the glenoid implant 310 of the present disclosure is now described. A block of material (e.g., a cube of plastic) is provided and milled into a stock glenoid component. The stock glenoid component has the body 320 with the concave surface 322, the convex surface 324, and the edge surface 326. The block of material is further milled such that the stock glenoid component further includes the central peg 330 extending from the central area 325a of the convex surface 324. The block of material is further milled such that the stock glenoid component further includes three peripheral peg blanks extending from and integral with (i.e., monolithic) the peripheral area 325b of the convex surface 324. Each of the peripheral peg blanks is generally a cylindrical piece of material. Each of the peripheral peg blanks is milled, using one or more tools 500 (FIG. 6A), to form a portion of the cylindrically shaped body 351, the tip portion 352, and a generally cylindrical portion 400, as shown in FIG. 6B.

Figure 6D:
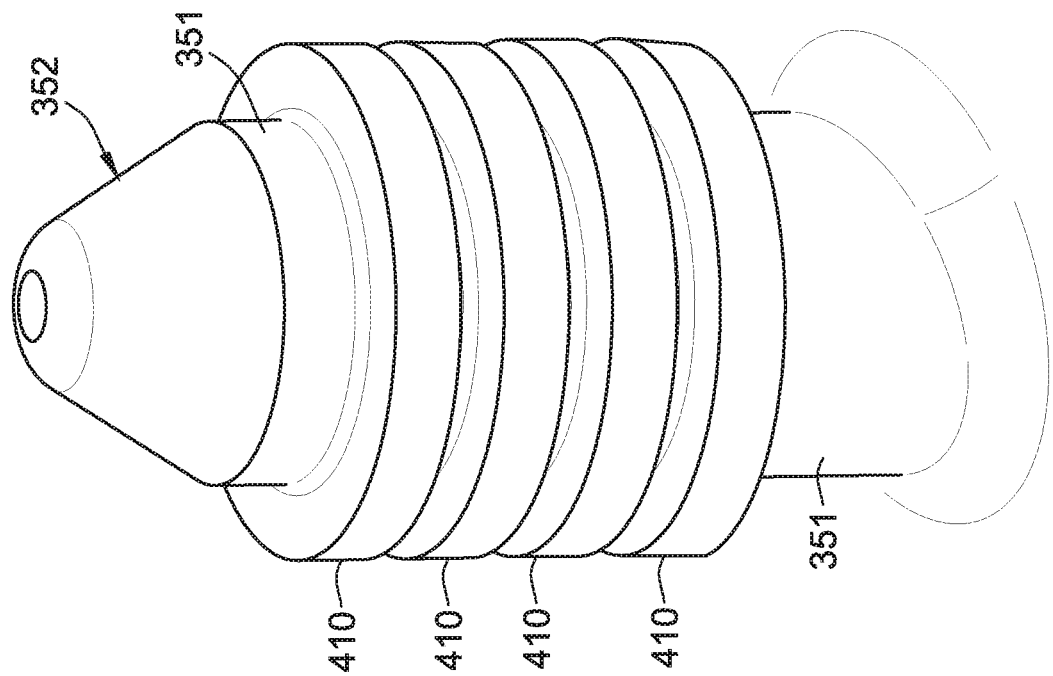
FIG. 6D is a perspective view of the modified peripheral peg of FIG. 6C having the plurality of radially extending disk features.
Figure 6C:
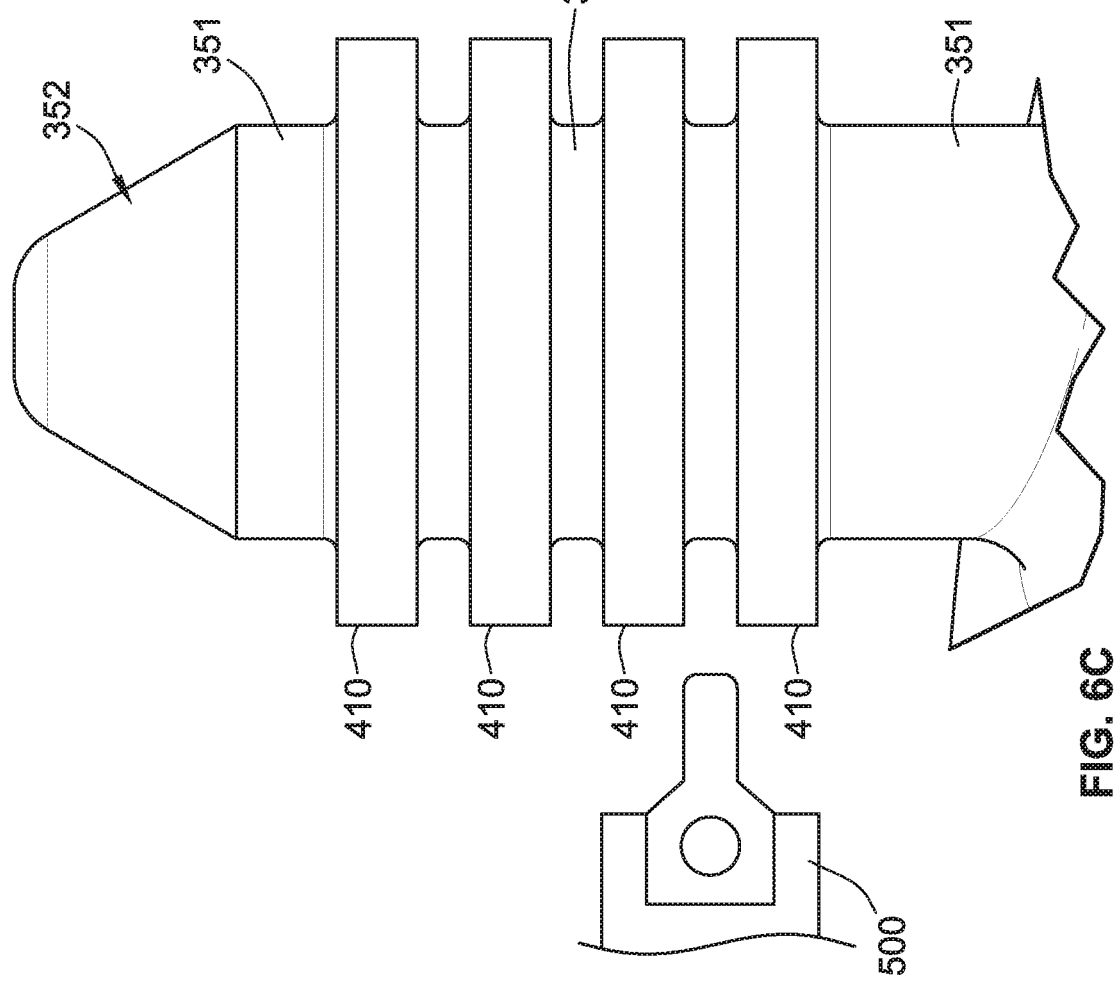
FIG. 6C is a side view illustrating a tool modifying the partially formed version of the peripheral peg of FIG. 6B by creating a plurality of radially extending disk features therein.
Figure 6F:
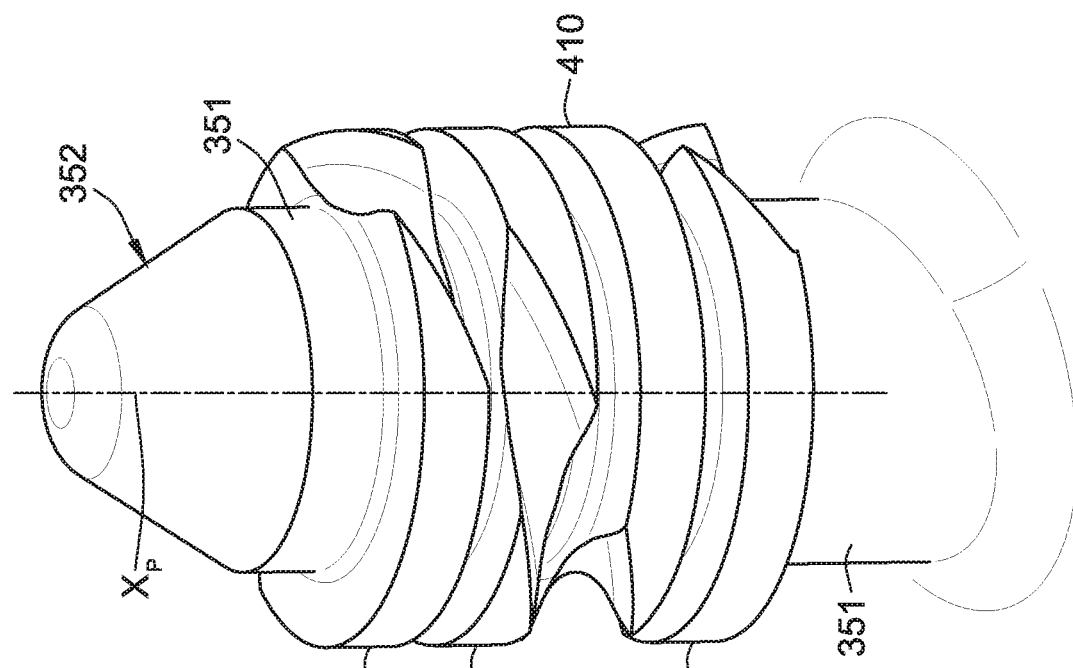
FIG. 6F is a perspective view of the modified peripheral peg of FIG. 6E having the plurality of radially extending disk features with a helical groove cut therein.
Figure 6E:
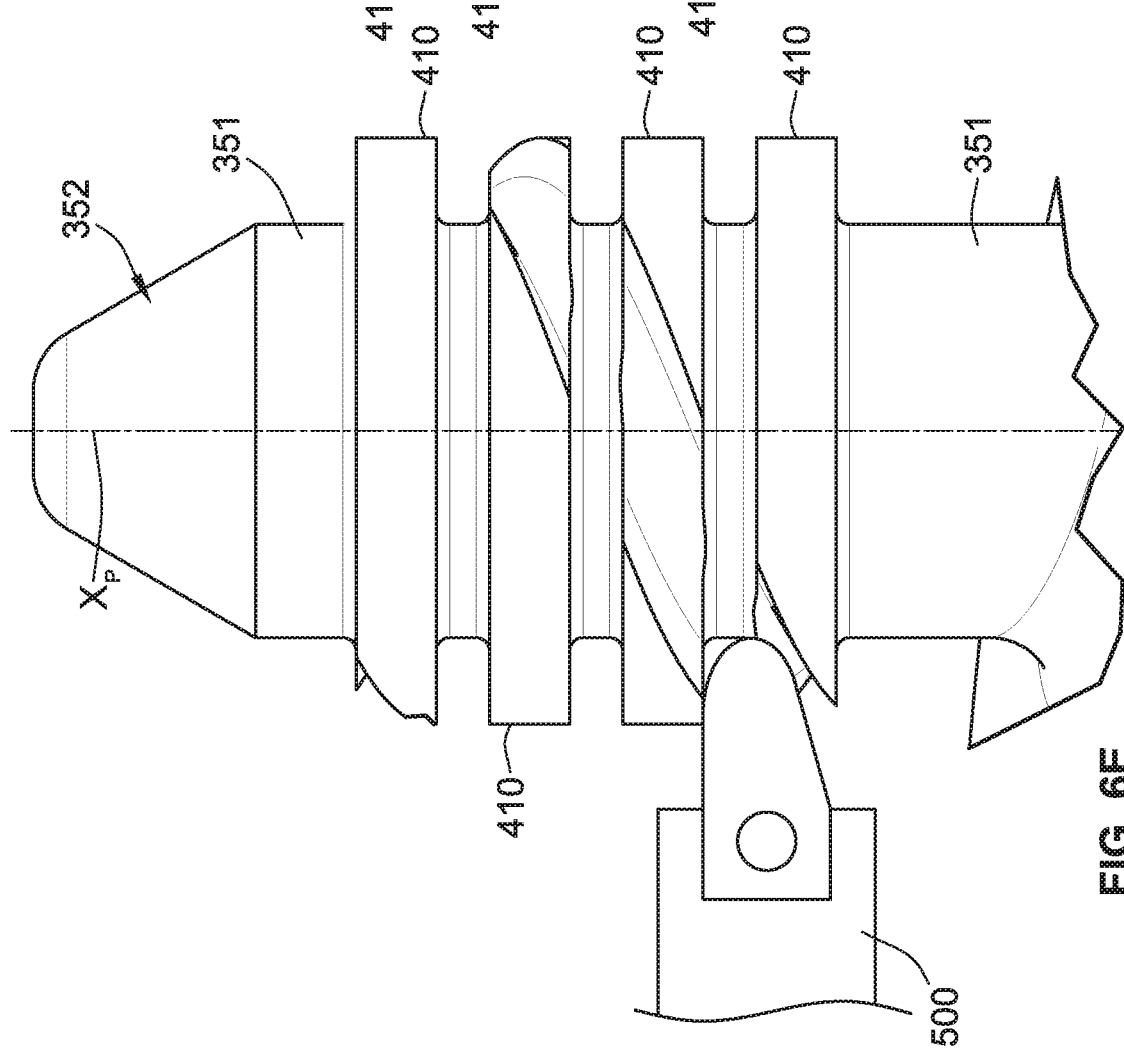
FIG. 6E is a side view illustrating a tool creating a helical groove in the plurality of radially extending disk features of the modified peripheral peg of FIG. 6D.
Figure 6H:
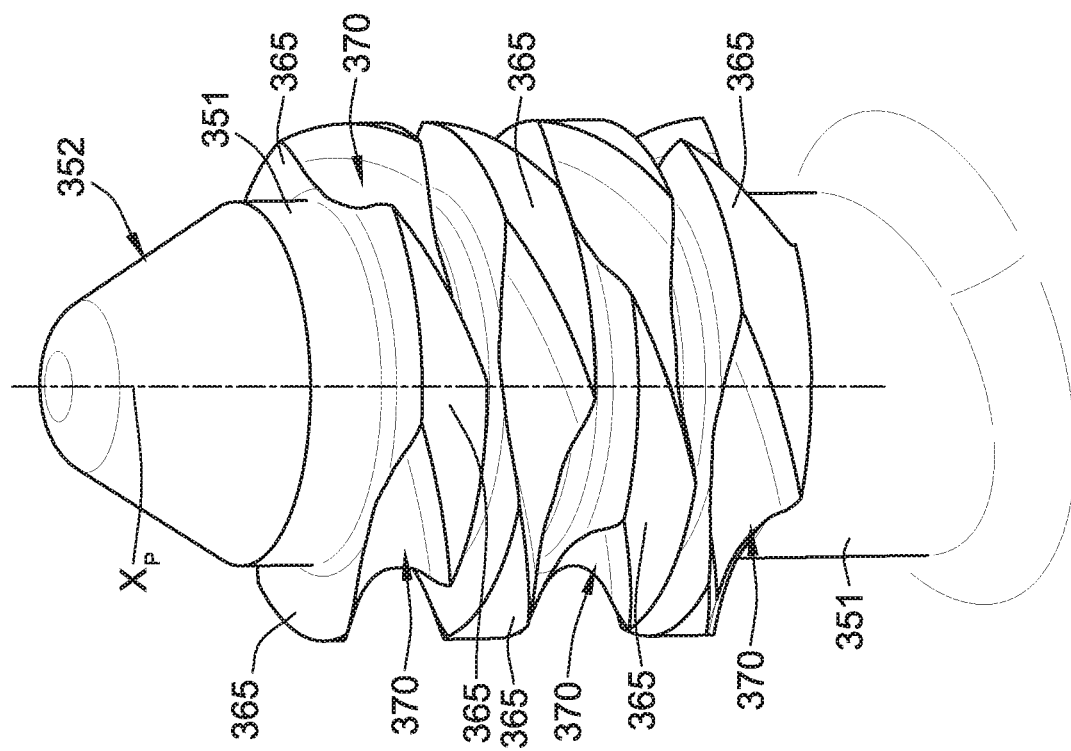
FIG. 6H is a perspective view of the modified peripheral peg of FIG. 6G having the plurality of radially extending disk features with the helical groove and the second helical groove cut therein thereby forming each of the plurality of radially extending disk features into three resilient lobes according to some implementations of the present disclosure.
Figure 6G:
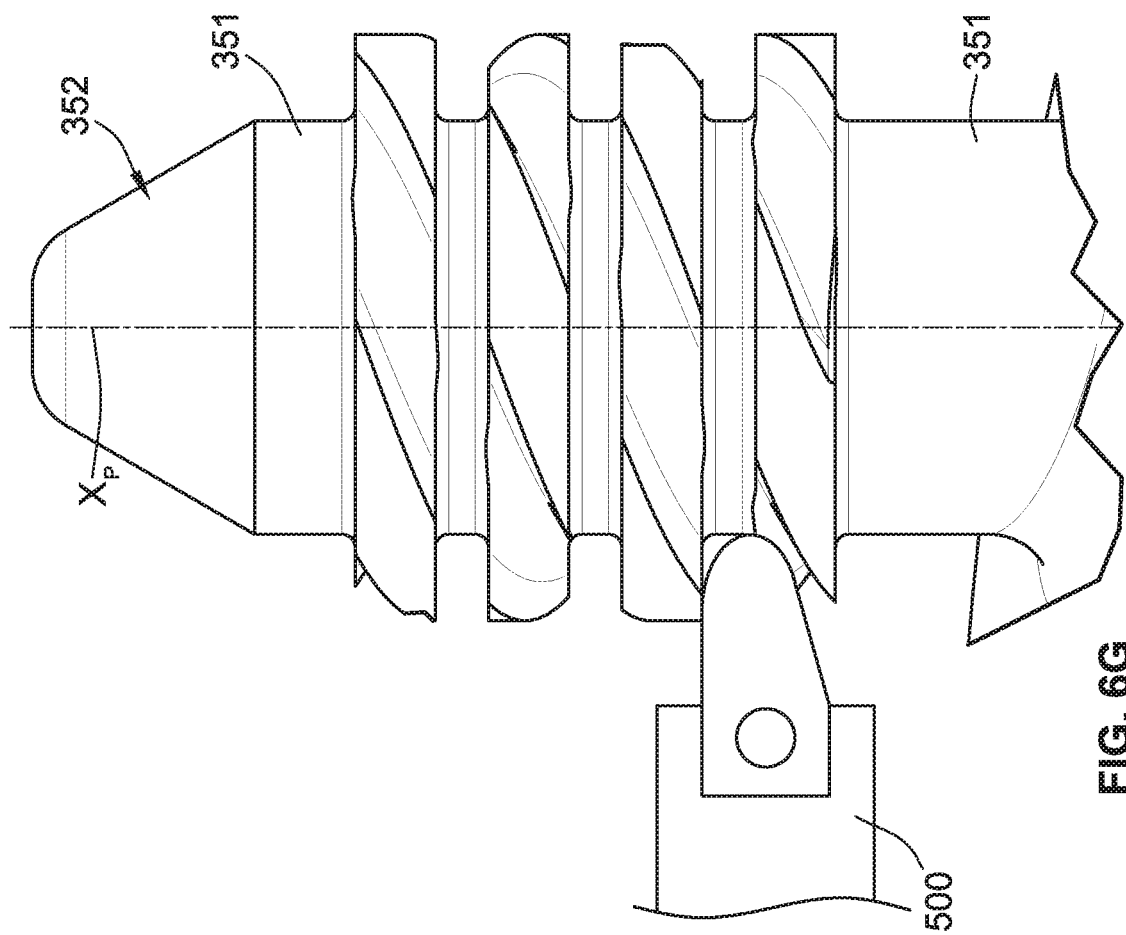
FIG. 6G is a side view illustrating a tool creating a second helical groove in the plurality of radially extending disk features of the modified peripheral peg of FIG. 6F.

With the peripheral peg blanks so formed (FIG. 6B), the generally cylindrical portion 400 of the peripheral peg blanks is cut and/or milled, using one or more tools 500 (FIG. 6C), to create a portion of the cylindrically shaped body 351 and a multitude of radially extending disks 410 that extend from the cylindrically shaped body 351, as shown in FIGS. 6C and 6D. With the radially extending disks 410 so formed, one or more tools 500 (FIGS. 6E and 6G) is moved in one or more helical paths with respect to the central axis $X_P$ of the peripheral peg blank to cut and/or mill the created radially extending disks 410, thereby modifying each of the radially extending disks 410 to have the three lobes 365 (FIG. 6H). In some such implementations, the one or more tools 500 are moved in three separate and distinct helical paths with respect to the central axis $X_P$ of the peripheral peg blank to create the helical channels 370 and the three lobes 365 of each of the radially extending features 360.

Alternatively to the one or more tools 500 being moved in one or more helical paths, the one or more tools 500 and/or or one or more different tools can be moved in a variety of other paths to cut and/or mill each of the created radially extending disks 410 into three separate and distinct lobes. In some such implementations, the one or more tools 500 are moved vertically with respect to the central axis $X_P$ of the peripheral peg blank to create and/or cut three vertical channels (not shown) in a first one of the radially extending disks 410. As such, the three vertical channels in the first radially extending disk 410 have a first rotational orientation. Then the one or more tools are repositioned and moved vertically with respect to the central axis $X_P$ of the peripheral peg blank to create and/or cut three vertical channels (not shown) in a second one of the radially extending disks 410 such that the three vertical channels in the second radially extending disk 410 are angularly offset from the three vertical channels created in the first radially extending disk 410. This process can continue for the other radially extending disks 410 such that each of the radially extending disks 410 is cut into three lobes or three portions where the three lobes of each radially extending disk 410 are angularly offset as compared with the three lobes created in the other radially extending disks 410.

Any tool or tools are contemplated for use in making/creating the glenoid implant 310, such as, for example, a milling machine, a lathe machine, a burr, a drill bit, a threaded die, a multi-lead threaded die, a robotic arm, a chisel, or any combination thereof.

Now referring to FIGS. 7A-7I, the humeral stem implant 110 includes a lower stem portion 120, an upper stem portion 130, a first pair of fins 140a, a second pair of fins 140b, and a biologic ingrowth coating 180. The lower stem portion 120 includes a generally cylindrical portion 122 that has a central axis, $X_S$, which is also referred to generally as the central axis of the lower stem portion 120 or as the central axis of the humeral stem implant 110. The lower stem portion 120 is generally smooth and free from the biologic ingrowth coating 180.

The upper stem portion 130 extends from the lower stem portion 120. In some implementations, the upper stem portion 130 and the lower stem portion 120 are monolithic and formed from the same block of material. The upper stem portion 130 has the tapered face 132 that is angled relative to the central axis, $X_S$, of the lower stem portion 120. The angle of the tapered face 132 relative to the central axis, $X_S$, of the lower stem portion 120 is between about fifteen degrees to about seventy-five degrees. In some implementations, the angle of the tapered face 132 relative to the central axis, $X_S$, of the lower stem portion 120 is between about thirty degrees to about sixty degrees. In some implementations, the angle of the tapered face 132 relative to the central axis, $X_S$, of the lower stem portion 120 is about forty-five degrees.

The interior bore 135 (FIGS. 2A, 7A, and 7C) is formed in the upper stem portion 130. As described above, the interior bore 135 is for engaging the first end portion 212a (FIGS. 2A and 2B) of the humeral neck implant component 210 in a taper lock configuration (e.g., a morse taper lock). The interior bore 135 extends inward from the tapered face 132 and tapers inwardly in an inward direction along a central axis of the interior bore 135 from the tapered face 132.

While the humeral stem implant 110 can be installed in both the prepared left humerus bone of a patient and the prepared right humerus bone of a patient, the discussion below assumes that the humeral stem implant 110 is installed in a prepared left humerus bone of a patient. The first pair of fins 140a is coupled to a posterior portion 130a of an exterior surface of the upper stem portion 130 and the second pair of fins 140b is coupled to an anterior portion 130b of the exterior surface of the upper stem portion 130. Further, in a medial direction from the central axis $X_S$, a medial portion 130c of the exterior surface of the upper stem portion 130 is positioned between the posterior portion 130a and the anterior portion 130b and in a lateral direction from the central axis $X_S$, a lateral portion 130d (FIG. 7B) of the exterior surface of the upper stem portion 130 is positioned between the posterior portion 130a and the anterior portion 130b.

Figure 7A:
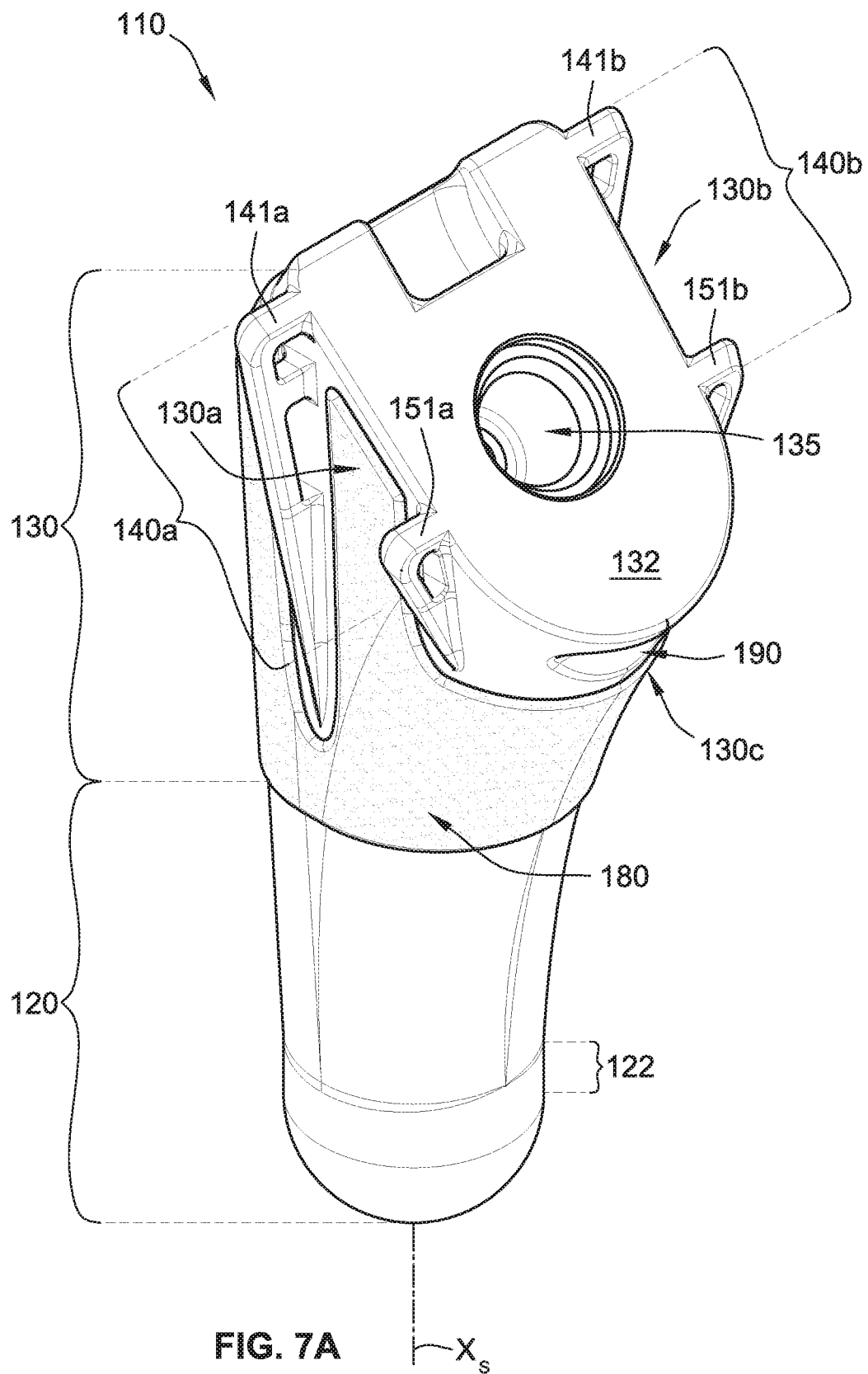
FIG. 7A is a front or medial perspective view of a humeral stem implant of the shoulder implant system of FIG. 1A according to some implementations of the present disclosure.
Figure 7B:
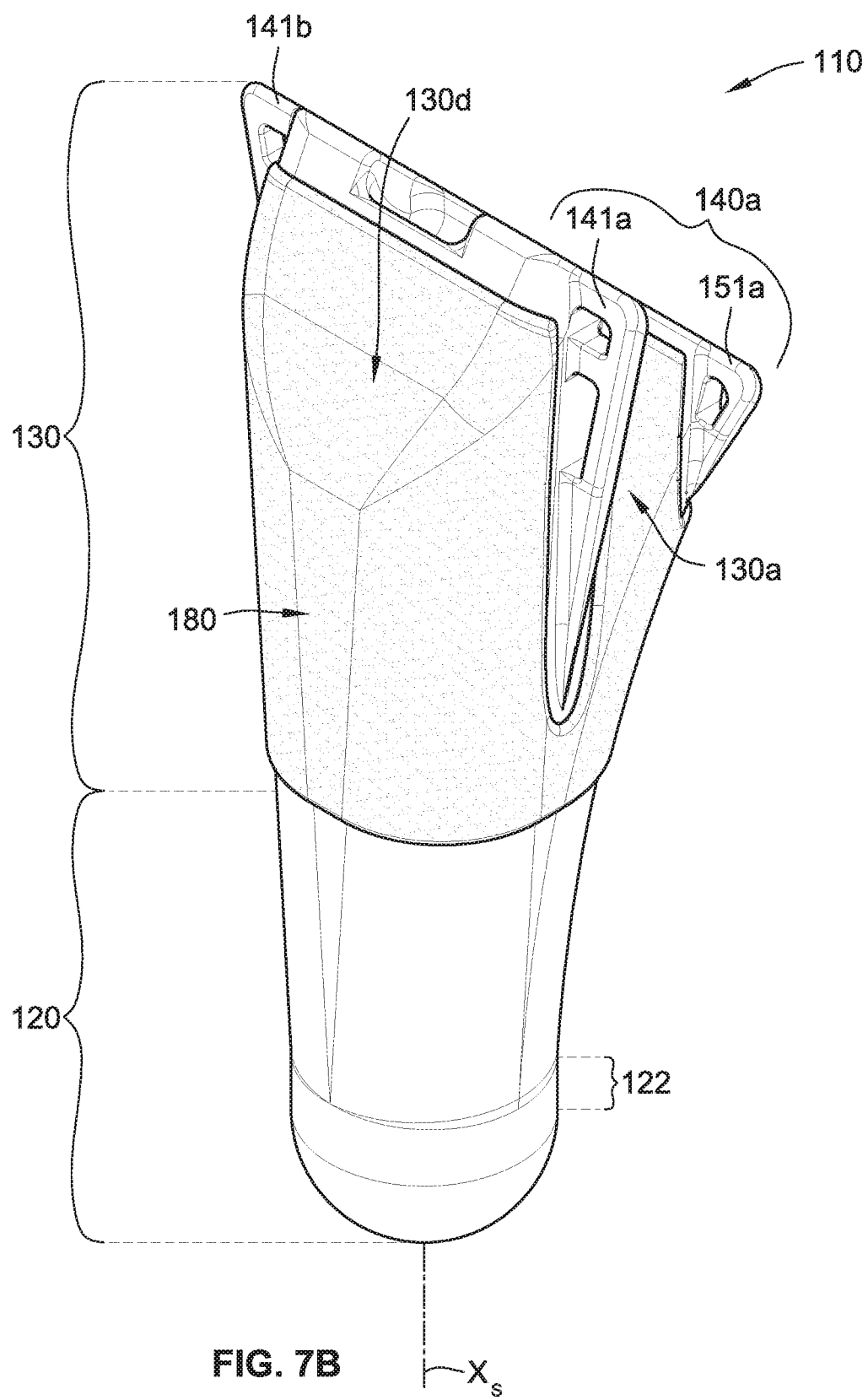
FIG. 7B is a rear or lateral perspective view of the humeral stem implant of FIG. 7A.
Figure 7C:
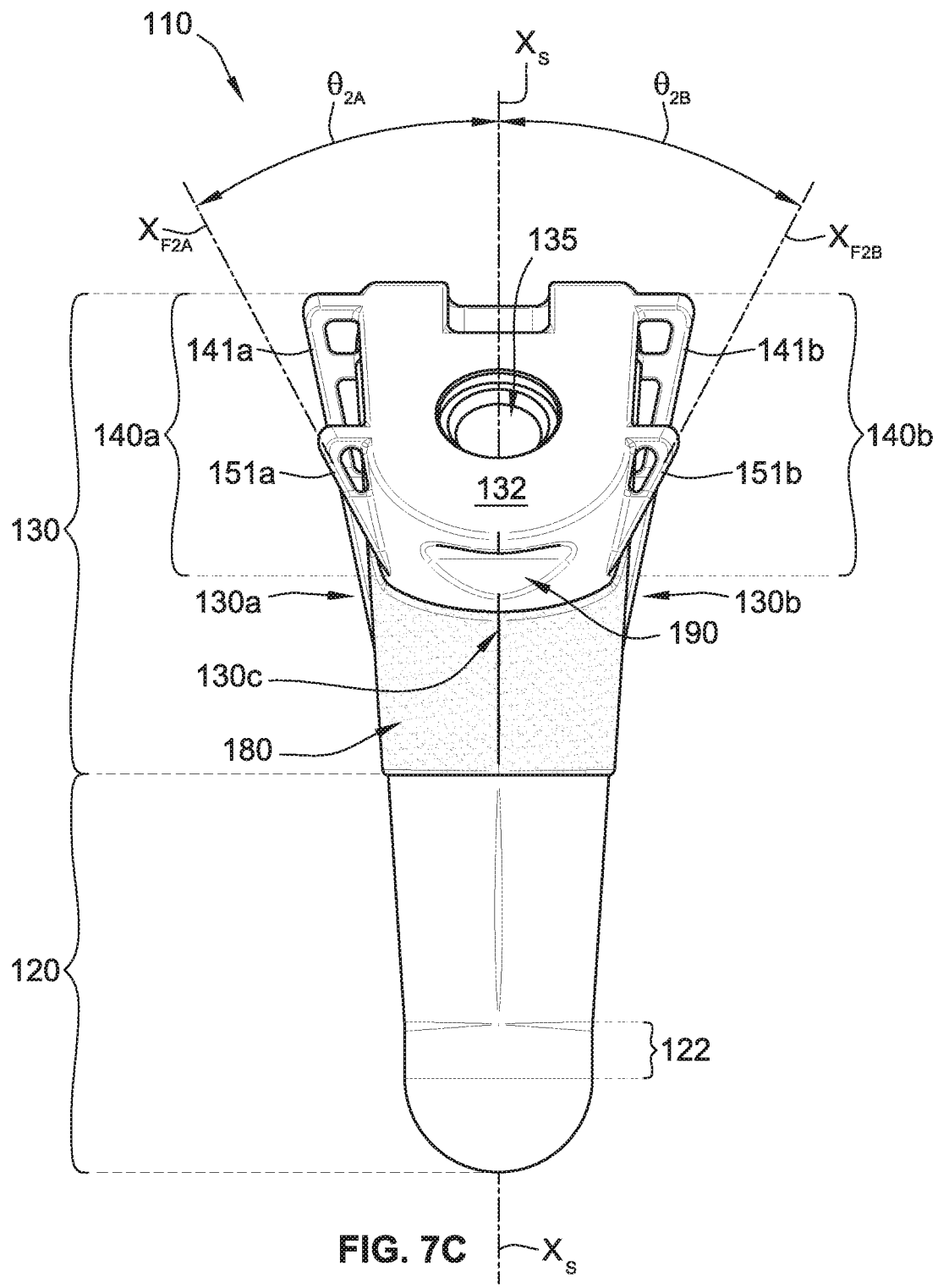
FIG. 7C is a front or medial plan view of the humeral stem implant of FIG. 7A.
Figure 7D:
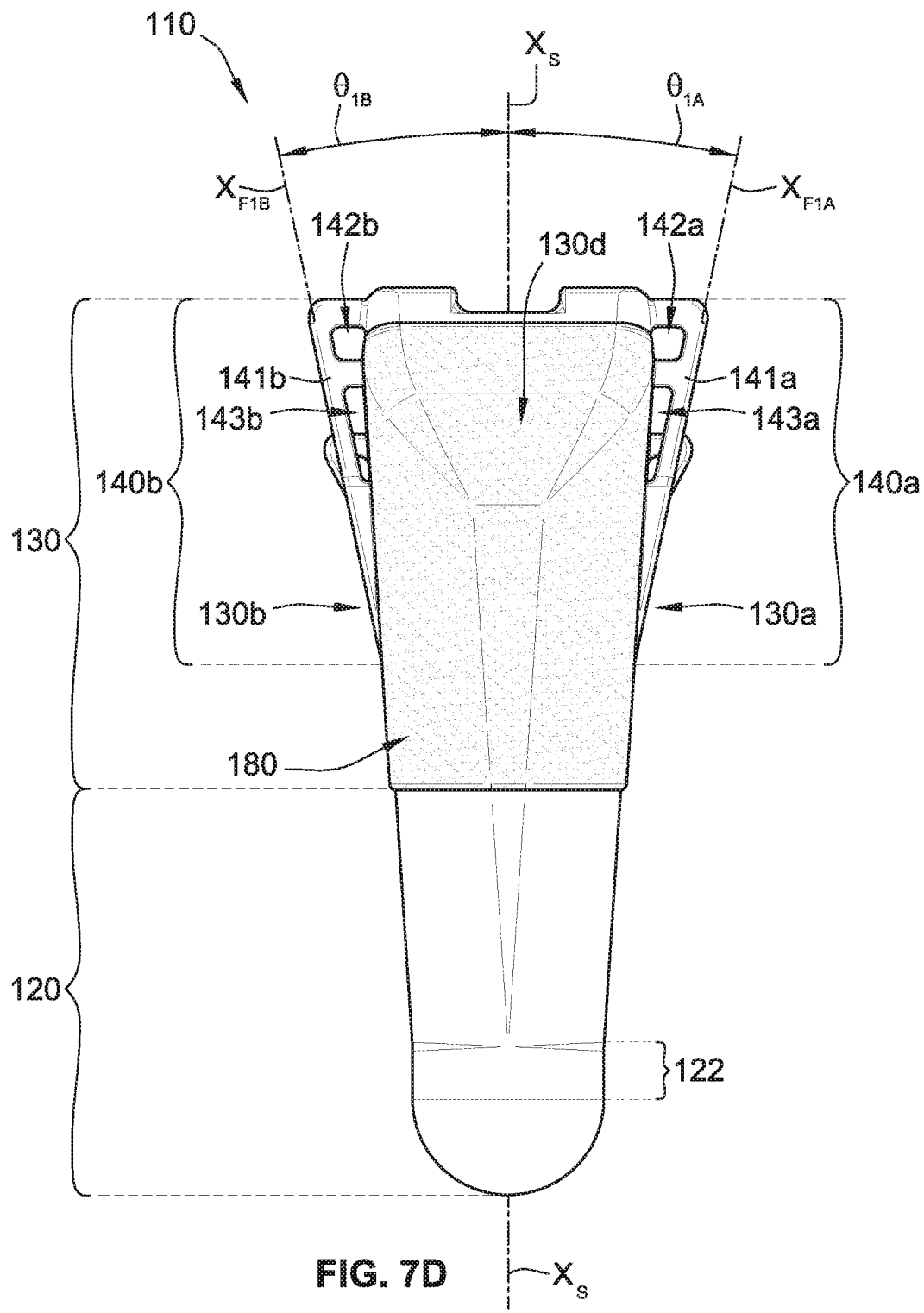
FIG. 7D is a rear or lateral plan view of the humeral stem implant of FIG. 7A.

As best shown in FIGS. 7C and 7D, the first pair of fins 140a includes a first fin 141a and a second fin 151a. Similarly, the second pair of fins 140b includes a first fin 141b and a second fin 151b. The second pair of fins 140b is a mirror image of the first pair of fins 140a over a central plane bisecting the humeral stem implant 110 through the central axis $X_S$. Although in some implementations, the second pair of fins 140b differs from the first pair of fins 140a.

Figure 7E:
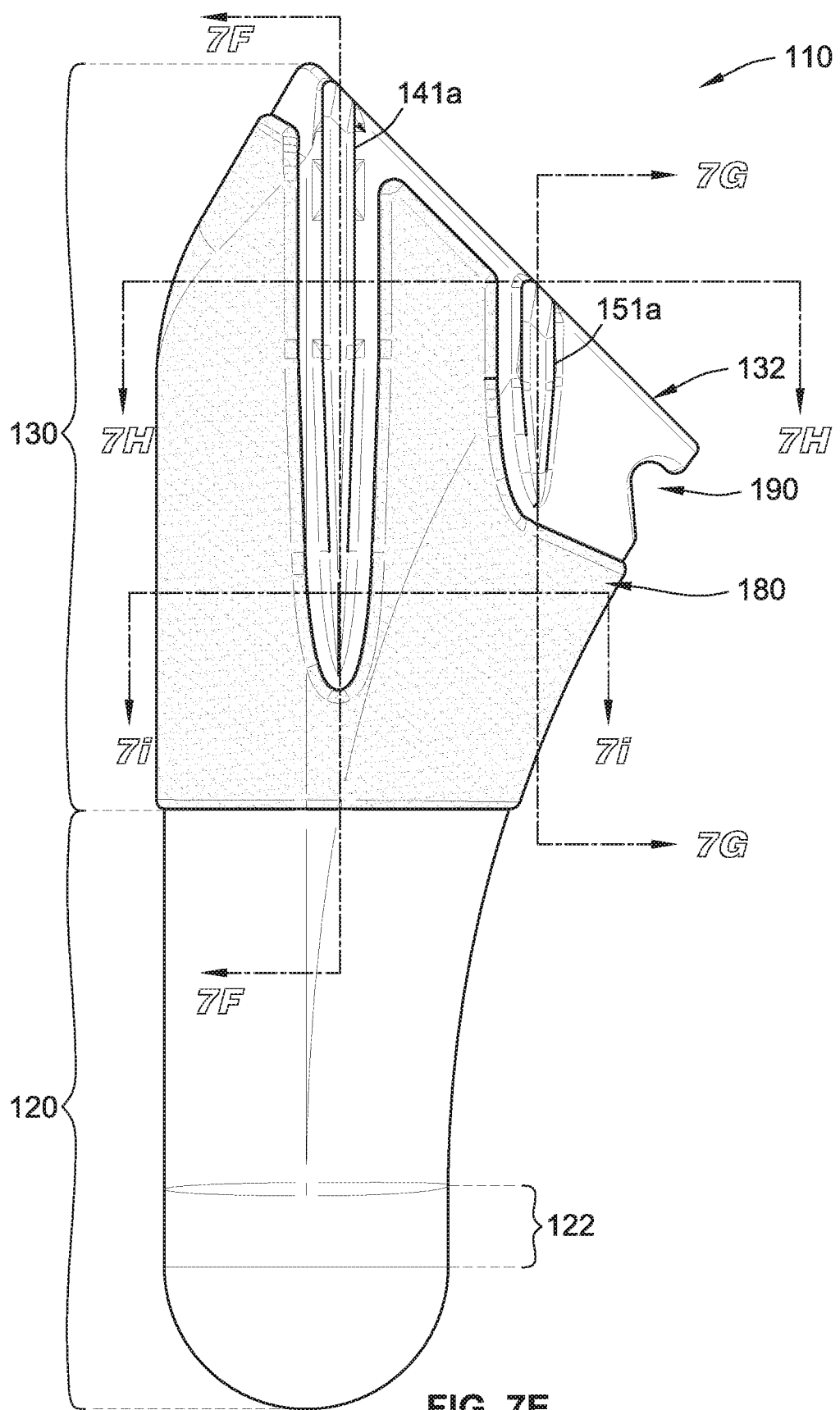
FIG. 7E is a side (posterior or anterior) plan view of the humeral stem implant of FIG. 7A.
Figure 7F:
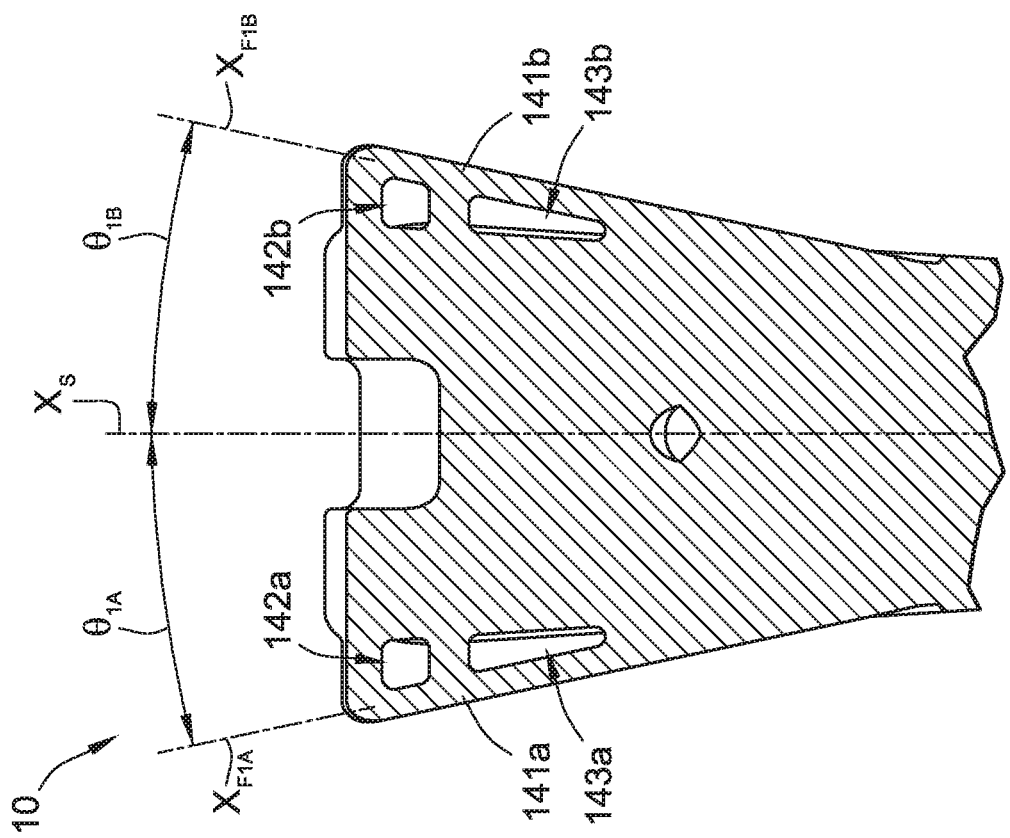
FIG. 7F is a partial cross-sectional view of the humeral stem implant of FIG. 7E taken at line 7F-7F.

As best shown in FIGS. 7D and 7F, the first fin 141a of the first pair of fins 140a has a central axis $X_{F1A}$, that is at an angle, $\theta_{1A}$, with respect to the central axis $X_S$, and/or vertical, where the angle, $\theta_{1A}$, can be any angle, such as, for example, between about five degrees and about thirty degrees. In some implementations, the angle, $\theta_{1A}$, is between about ten degrees and about fifteen degrees. Similarly, the first fin 141b of the second pair of fins 140b has a central axis $X_{F1B}$, that is at an angle, $\theta_{1B}$, with respect to the central axis $X_S$, and/or vertical, where the angle, $\theta_{1B}$, can be any angle, such as, for example, between about five degrees and about thirty degrees. In some implementations, the angle, $\theta_{1B}$, is between about ten degrees and about fifteen degrees.

The first fin 141a of the first pair of fins 140a has a first height/length and is attached to the posterior portion 130a of an exterior surface of the upper stem portion 130 at three separate and distinct locations such that the first fin 141a is rigidly connected to the upper stem portion 130. Such a three point coupling also results in the first fin 141a forming two windows 142a and 143a that can receive a suture therethrough for use in suturing and/or pulling bone and/or flesh towards the humeral stem implant 110 during installation of the shoulder implant system 100. Alternatively or additionally, the two windows 142a and 143a also provide locations for bone to grow through, which can aid in retaining the humeral stem implant 110 in place.

Similarly, the first fin 141b of the second pair of fins 140b has a first height/length and is attached to the anterior portion 130b of an exterior surface of the upper stem portion 130 at three separate and distinct locations such that the first fin 141b is rigidly connected to the upper stem portion 130. Such a three point coupling also results in the first fin 141b forming two windows 142b and 143b that can receive a suture therethrough for use in suturing and/or pulling bone and/or flesh towards the humeral stem implant 110 during installation of the shoulder implant system 100. Alternatively or additionally, the two windows 142b and 143b also provide locations for bone to grow through, which can aid in retaining the humeral stem implant 110 in place.

The height/length of the first fin 141a and the first fin 141b can be between about twenty percent and about sixty percent of a total height of the humeral stem implant 110. In some implementations, the height/length of the first fin 141a and the first fin 141b is between about thirty percent and about fifty percent of the total height of the humeral stem implant 110. In some implementations, the height/length of the first fin 141a and the first fin 141b is about forty percent of the total height of the humeral stem implant 110. In some implementations, the height/length of the first fin 141a and the first fin 141b is between about fifteen millimeters and about forty millimeters. In some implementations, the height/length of the first fin 141a and the first fin 141b is between about twenty millimeters and about thirty millimeters. In some implementations, the height/length of the first fin 141a and the first fin 141b is about twenty-five millimeters.

Figure 7G:
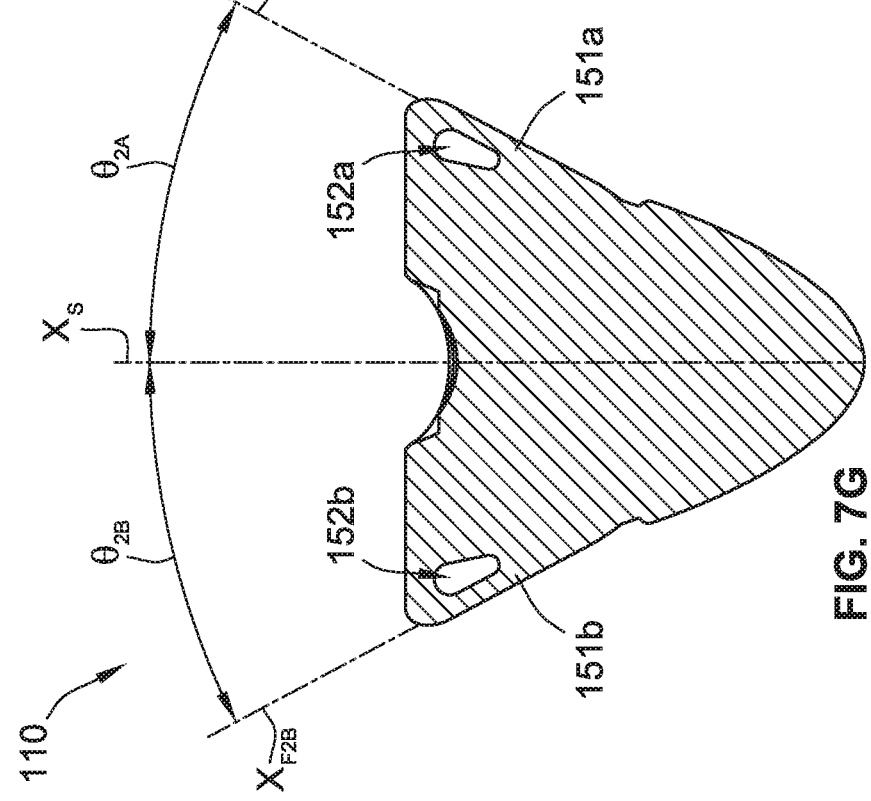
FIG. 7G is a cross-sectional view of the humeral stem implant of FIG. 7E taken at line 7G-7G.

As best shown in FIGS. 7C and 7G, the second fin 151a of the first pair of fins 140a has a central axis $X_{F2A}$, that is at an angle, $\theta_{2A}$, with respect to the central axis $X_S$, and/or vertical, where the angle, $\theta_{2A}$, can be any angle, such as, for example, between about twenty degrees and about forty degrees. In some implementations, the angle, $\theta_{2A}$, is between about twenty-five degrees and about thirty degrees. Similarly, the second fin 151b of the second pair of fins 140b has a central axis $X_{F2B}$, that is at an angle, $\theta_{2B}$, with respect to the central axis $X_S$, and/or vertical, where the angle, $\theta_{2B}$, can be any angle, such as, for example, between about twenty degrees and about forty degrees. In some implementations, the angle, $\theta_{2B}$, is between about twenty-five degrees and about thirty degrees.

The differing angles of the first fins 141a, 141b as compared to the second fins 151a, 151b aids in preventing rotation of the humeral stem implant 110 when positioned in a humeral cavity of the prepared humerus bone of the patient by engaging cancellous bone at varying angles.

The second fin 151a of the first pair of fins 140a has a second height/length (e.g., that is smaller than the first height of the first fin 141a) and is attached to the posterior portion 130a of an exterior surface of the upper stem portion 130 at two separate and distinct locations such that the second fin 151a is rigidly connected to the upper stem portion 130. Such a two point coupling also results in the second fin 151a forming one window 152a that can receive a suture therethrough for use in suturing and/or pulling bone and/or flesh towards the humeral stem implant 110 during installation of the shoulder implant system 100. Alternatively or additionally, the window 152a also provides a location for bone to grow through, which can aid in retaining the humeral stem implant 110 in place.

Similarly, the second fin 151b of the second pair of fins 140b has a second height/length (e.g., that is smaller than the first height of the first fin 141b) and is attached to the anterior portion 130b of an exterior surface of the upper stem portion 130 at two separate and distinct locations such that the second fin 151b is rigidly connected to the upper stem portion 130. Such a two point coupling also results in the second fin 151b forming one window 152b that can receive a suture therethrough for use in suturing and/or pulling bone and/or flesh towards the humeral stem implant 110 during installation of the shoulder implant system 100. Alternatively or additionally, the window 152b also provides a location for bone to grow through, which can aid in retaining the humeral stem implant 110 in place.

The height/length of the second fin 151a and the second fin 151b can be between about five percent and about thirty-five percent of a total height of the humeral stem implant 110. In some implementations, the height/length of the second fin 151a and the second fin 151b is between about fifteen percent and about twenty-five percent of the total height of the humeral stem implant 110. In some implementations, the height/length of the second fin 151a and the second fin 151b is about twenty percent of the total height of the humeral stem implant 110. In some implementations, the height/length of the second fin 151a and the second fin 151b is between about five millimeters and about twenty millimeters. In some implementations, the height/length of the second fin 151a and the second fin 151b is between about ten millimeters and about fifteen millimeters. In some implementations, the height/length of the second fin 151a and the second fin 151b is about twelve millimeters.

Figure 7H:
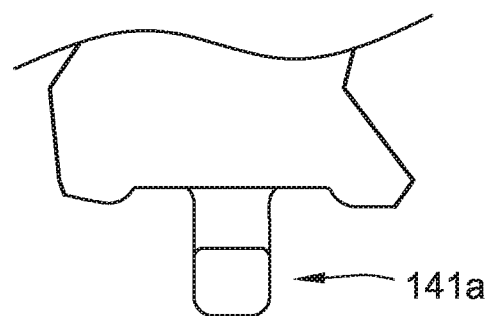
FIG. 7H is a partial cross-sectional view of the humeral stem implant of FIG. 7E taken at line 7H-7H.
Figure 7I:
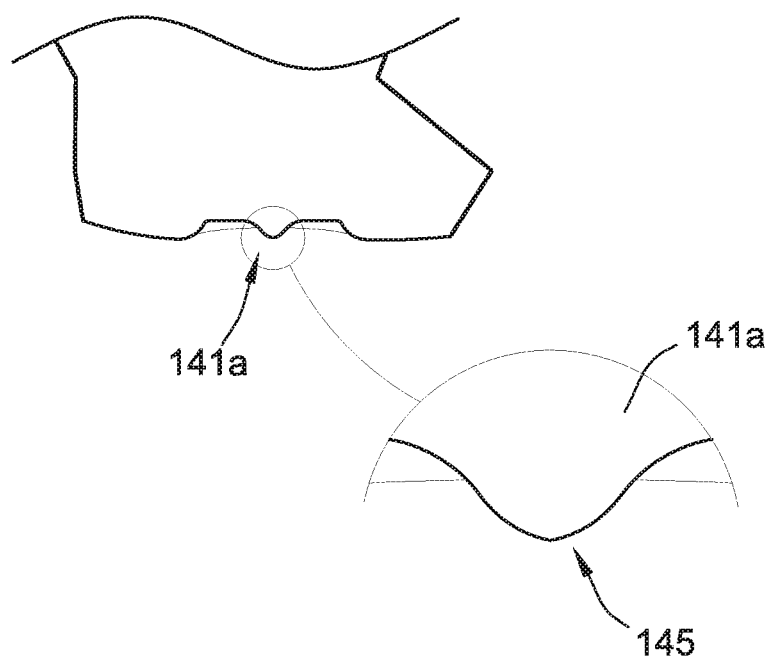
FIG. 7I is a partial cross-sectional view of the humeral stem implant of FIG. 7E taken at line 7I-7I.

As best shown in FIGS. 7H and 7I, which are cross-sectional views through the first fin 141a (FIG. 7E) at two different heights along the first fin 141a to illustrate the difference in the body of the first fin 141a along its height/length. Specifically, an upper portion of the first fin 141a has a generally square cross-sectional with rounded corners (FIG. 7H), whereas the lower portion of the first fin 141a has a wedge shaped cross-section with a rounded edge 145 (FIG. 7I). As such, the wedge shape of the lower portion of the first fin 141a directly engages and compacts cancellous bone in the prepared humeral bone of the patient during installation of the humeral stem implant 110. When the humeral stem implant 110 is fully installed (e.g., the tapered face 132 is about flush with the cut humerus bone or the osteotomy cut surface), such a compacting of the cancellous bone by the first fin 141a aids in preventing rotation of the humeral stem implant 110. Similarly, portions (e.g., lower portions) of the first fin 141b and of the second fin 151a and the second fin 151b, can include the same, or similar, wedge shape to also engage and compact cancellous bone. Further, the entire body of each of the fins 141a, 141b, 151a, 151b can have a wedge shaped cross-section. In some implementations, the wedge shaped cross-section forms a sharp edge or a knife edge (e.g., instead of the rounded edge 145) to aid in the cutting of cancellous bone during installation of the humeral stem implant 110.

As best shown in FIGS. 7A-7D, the biologic ingrowth coating 180 is attached to a majority portion of the exterior surface of the upper stem portion 130. In some implementations, the biologic ingrowth coating 180 extends downward from the tapered face 132 and past or beyond the first fin 141a and the first fin 141b. In some implementations, the biologic ingrowth coating 180 extends downward from the tapered face 132 and at least 1 millimeter past or beyond the first fin 141a and the first fin 141b. As shown, the biologic ingrowth coating 180 is not attached to the tapered face 132, the lower stem portion 120, the first pair of fins 140a, and the second pair of fins 140b. Alternatively, the biologic ingrowth coating 180 may be attached to a portion of one or more of: (i) the tapered face 132, (ii) the lower stem portion 120, (iii) the first pair of fins 140a, and (iv) the second pair of fins 140b. The biologic ingrowth coating 180 is a very porous material that is attached generally to the upper stem portion 130. In some implementations, the biologic ingrowth coating 180 is a porous, porous material where the pores of the material also have pores. The biologic ingrowth coating 180 is generally attached to the humeral stem implant 110 to promote osseointegration of the humeral stem implant 110 with the prepared humeral bone of the patient.

In some implementations, the upper stem portion 130 of the humeral stem implant 110 includes a notch 190 (FIGS. 7A, 7C, and 7E). The notch 190 is positioned adjacent to (e.g., below) the tapered face 132 in the medial portion 130c of the exterior surface of the upper stem portion 130. The notch 190 is sized and shaped to be engaged by a tip of a stem extractor tool (not shown) to remove the humeral stem implant 110 from the humeral canal of the prepared humerus bone of the patient subsequent to being seated/installed therein.

It is expressly contemplated that any element or elements from any one or more of the claims enumerated herein can be combined with any other element or elements in any of the other claims to form a contemplated implementation of the present disclosure.

Each of the above implementations and obvious variations thereof is contemplated as falling within the spirit and scope of the claimed invention, which is set forth in the following claims.

What is claimed is:

1. A humeral stem implant, comprising:
a lower stem portion having a central axis;
an upper stem portion extending from the lower stem portion, the upper stem portion having a tapered face that is angled relative to the central axis of the lower stem portion;
a first pair of parallel fins being coupled to a posterior portion of an exterior surface of the upper stem portion at multiple distinct locations such that each fin of the first pair of parallel fins forms one or more windows, wherein the first pair of parallel fins comprises a first fin and a second fin, wherein the first fin deviates from the central axis at a first angle and the second fin deviates from the central axis at a second angle, wherein the first angle is smaller than the second angle, wherein the first fin extends from a lateral half of the tapered face and the second fin extends from a medial half of the tapered face, wherein the first fin includes a first window and a second window wherein the first window is larger than the second window, wherein the second fin includes a third window, and wherein the second angle is between twenty degrees and forty degrees; and
a second pair of parallel fins being coupled to an anterior portion of the exterior surface of the upper stem portion,
wherein the first pair of parallel fins and the second pair of parallel fins are configured to provide rotational stability to the humeral stem implant by directly engaging cancellous bone responsive to the humeral stem implant being seated in a humeral canal of a prepared humerus bone of a patient.

2. The humeral stem implant of claim 1, wherein at least a portion of a posterior surface of each of the first pair of parallel fins forms a wedge and wherein at least a portion of an anterior surface of each of the second pair of parallel fins forms a respective wedge.

3. The humeral stem implant of claim 1, wherein each of the first pair of parallel fins and each of the second pair of parallel fins tapers inwardly relative to the central axis of the lower stem portion, and wherein the inward taper of each of the first pair of parallel fins and the inward taper of each of the second pair of parallel fins extends inwardly in a downward direction from the upper stem portion towards the lower stem portion.

4. The humeral stem implant of claim 1, wherein the first fin has a first length and the second fin has a second length that is less than half of the first length, and wherein a first one of the second pair of parallel fins has a third length that is about equal to the first length and a second one of the second pair of parallel fins has a fourth length that is about equal to the second length.

5. The humeral stem implant of claim 1, wherein the one or more windows are configured to receive a respective suture therethrough and wherein each of the second pair of parallel fins forms a respective window therein that is configured to receive a respective suture therethrough.

6. The humeral stem implant of claim 1, further comprising a biologic ingrowth coating attached to a majority portion of the exterior surface of the upper stem portion such that the biologic ingrowth coating extends downward from the tapered face at least one millimeter beyond the first and the second pairs of parallel fins, and wherein the biologic ingrowth coating is not attached to the tapered face, the lower stem portion, the first pair of parallel fins, and the second pair of parallel fins.

7. The humeral stem implant of claim 1, further comprising a notch positioned adjacent to the tapered face in a medial portion of the exterior surface of the upper stem portion, the notch being configured to be engaged by a tip of a stem extractor tool for removing the humeral stem implant from the humeral canal of the prepared humerus bone of the patient subsequent to being seated therein.

8. A humeral stem implant, comprising:
a lower stem portion having a central axis;
an upper stem portion extending from the lower stem portion, the upper stem portion having a tapered face that is angled relative to the central axis of the lower stem portion;
a first longitudinal fin having a first central axis and a first length and being coupled to a posterior portion of an exterior surface of the upper stem portion at multiple distinct locations such that the first longitudinal fin forms a first window and a second window that are configured to receive a suture therethrough, wherein the first window is larger than the second window, the first longitudinal fin tapering inwardly such that the first central axis is at a first angle relative to the central axis of the lower stem portion, wherein the first longitudinal fin is a lateral-most longitudinal fin, and wherein the first longitudinal fin extends from a lateral half of the tapered face;
a second longitudinal fin having a second central axis and a second length and being coupled to the posterior portion of the exterior surface of the upper stem portion at multiple distinct locations such that the second longitudinal fin forms a third window that is configured to receive a suture therethrough, the second longitudinal fin tapering inwardly such that the second central axis is at a second angle relative to the central axis of the lower stem portion, the first angle being smaller than the second angle, the second angle being between twenty degrees and forty degrees, the second length being less than half of the first length, the first longitudinal fin and the second longitudinal fin being configured to provide rotational stability to the humeral stem implant by directly engaging cancellous bone responsive to the humeral stem implant being seated in a humeral canal of a prepared humerus bone of a patient, wherein the second longitudinal fin extends from a medial half of the tapered face; and
a biologic ingrowth coating attached to a majority portion of the exterior surface of the upper stem portion such that the biologic ingrowth coating extends downward from the tapered face at least one millimeter beyond the first longitudinal fin.

9. The humeral stem implant of claim 8, wherein at least a portion of a posterior surface of the first longitudinal fin is tapered to form a wedge that directly engages and compacts cancellous bone during installation of the humeral stem implant.

10. The humeral stem implant of claim 8, wherein the lower stem portion is configured to extend into a transition zone between a metaphysis and a diaphysis of the prepared humerus bone of the patient responsive to the humeral stem implant being seated in the humeral canal with the tapered face of the upper stem portion being about flush with an osteotomy cut of the prepared humerus bone, and wherein the lower stem portion is configured such that the lower stem portion does not contact cortical bone of the prepared humerus bone of the patient responsive to the humeral stem implant being seated in the humeral canal with the tapered face of the upper stem portion being about flush with an osteotomy cut of the prepared humerus bone.

11. The humeral stem implant of claim 8, further comprising:
a third longitudinal fin having a third central axis and a third length and being coupled to an anterior portion of the exterior surface of the upper stem portion such that the third longitudinal fin forms a fourth window that is configured to receive a suture therethrough, the third length being generally the same as the first length of the first longitudinal fin, the third longitudinal fin tapering inwardly such that the third central axis is at the first angle relative to the central axis of the lower stem portion;
a fourth longitudinal fin having a fourth central axis and a fourth length and being coupled to the anterior portion of the exterior surface of the upper stem portion such that the fourth longitudinal fin forms a fifth window that is configured to receive a suture therethrough, the fourth length being generally the same as the second length of the second longitudinal fin, the fourth longitudinal fin tapering inwardly such that the fourth central axis is at the second angle relative to the central axis of the lower stem portion, the third longitudinal fin and the fourth longitudinal fin being configured to further provide rotational stability to the humeral stem implant by directly engaging cancellous bone responsive to the humeral stem implant being seated in the humeral canal of the prepared humerus bone of the patient.

12. The humeral stem implant of claim 8, wherein the first longitudinal fin is coupled to the posterior portion of the exterior surface of the upper stem portion at three distinct locations such that the first longitudinal fin forms the first window and the second window.

13. A humeral stem implant, comprising:
a lower stem portion having a central axis;
an upper stem portion extending from the lower stem portion, the upper stem portion having a tapered face that is angled relative to the central axis of the lower stem portion;
a first elongated fin coupled to an exterior surface of the upper stem portion at multiple distinct locations such that the first elongated fin includes a first window and a second window wherein the first window is larger than the second window, the first elongated fin being inwardly tapered at a first angle relative to the central axis of the lower stem portion, at least a portion of the first elongated fin forming a first wedge that directly engages and compacts cancellous bone during installation of the humeral stem implant, the first elongated fin being a lateral-most elongated fin, wherein the first elongated fin extends from a lateral half of the tapered face; and
a second elongated fin coupled to the exterior surface of the upper stem portion, the second elongated fin being inwardly tapered at a second angle relative to the central axis of the lower stem portion, wherein the first angle is smaller than the second angle and the second angle is between twenty degrees and forty degrees, at least a portion of the second elongated fin forming a second wedge that directly engages and compacts cancellous bone during installation of the humeral stem implant, wherein the second elongated fin extends from a medial half of the tapered face, and wherein the second elongated fin includes a third window.

14. The humeral stem implant of claim 13, wherein the first elongated fin and the second elongated fin are both coupled to a posterior portion or an anterior portion of the external surface of the upper stem portion.

15. The humeral stem implant of claim 14, wherein a length of the second elongated fin is less than half of a length of the first elongated fin.

16. The humeral stem implant of claim 14, wherein the first elongated fin and the second elongated fin provide rotational stability to the humeral stem implant by directly engaging the cancellous bone responsive to the humeral stem implant being seated in a humeral canal of a prepared humerus bone of a patient.

17. The humeral stem implant of claim 13, wherein the first elongated fin is coupled to a posterior portion of the external surface of the upper stem portion and the second elongated fin is coupled to an anterior portion of the external surface of the upper stem portion.

18. The humeral stem implant of claim 17, wherein a length of the second elongated fin is about equal to a length of the first elongated fin.

* * * * *